(12) United States Patent
Von Der Kammer

(10) Patent No.: US 8,574,861 B2
(45) Date of Patent: Nov. 5, 2013

(54) PPM1E PROTEINS AND NUCLEIC ACIDS AS TARGETS FOR NEURODEGENERATIVE DISEASES

(75) Inventor: Heinz Von Der Kammer, Hamburg (DE)

(73) Assignee: Evotec AG, Hamburg (DE)

( * ) Notice: Subject to any disclaimer, the term of this patent is extended or adjusted under 35 U.S.C. 154(b) by 0 days.

(21) Appl. No.: 12/739,878

(22) PCT Filed: Oct. 24, 2008

(86) PCT No.: PCT/EP2008/064446
§ 371 (c)(1), (2), (4) Date: Apr. 26, 2010

(87) PCT Pub. No.: WO2009/053465
PCT Pub. Date: Apr. 30, 2009

(65) Prior Publication Data
US 2010/0261182 A1    Oct. 14, 2010

Related U.S. Application Data

(60) Provisional application No. 60/996,019, filed on Oct. 25, 2007.

(30) Foreign Application Priority Data

Oct. 25, 2007 (EP) .................................. 07119261

(51) Int. Cl.
*G01N 33/53* (2006.01)
*G01N 33/567* (2006.01)

(52) U.S. Cl.
USPC ............. 435/7.72; 435/6; 435/7.1; 435/7.21; 435/7.92; 436/501

(58) Field of Classification Search
None
See application file for complete search history.

(56) References Cited

PUBLICATIONS

International Search Report and Written Opinion with Form PCT/ISA/326 issued on Jan. 19, 2009, mailed on Feb. 26, 2009 for PCT Application No. PCT/EP2008/064446.
Kitani, Takako et al: "Post-translational excision of the carboxyl-terminal segment of CaM kinase phosphatase N and its cytosolic occurrence in the brain.". Journal of Neurochemistry Jan. 2006, vol. 96, No. 2, pp. 374-384.
Takeuchi Masayuki et al: "Identification and characterization of CaMKP-n, nuclear calmodulin-independent protein kinase phosphatase" Journal of Biochemistry (Tokyo), vol. 130, No. 6, Dec. 2001, pp. 833-840.
Ouchi, Toru et al: "Collaboration of signal transducer and activator of transcription 1 (STAT1) and BRCA1 in differential regulation of IFN-γ target genes" www.pnas.org, vol. 97, No. 10, May 9, 2000, pp. 5208-5213.
Sueyoshi Noriyuki et al: "Inhibitors of the Ca2+/calmodulin-dependent protein kinase phosphates family (CaMKP and CaMKP-N)" Biochemical and Biophysical Research Communications, vol. 363, No. 3, Nov. 2007, pp. 715-721.
Ishida A et al: "Identification of Major Ca<2+>/calmodulin-dependent protein kinase phosphatase-binding proteins in brain: biochemical analysis of the interaction" Archives of Biochemistry and Biophysics, New York, US, US, vol. 435, No. 1, Mar. 1, 2005, pp. 134-146.
Baloyannis, S.J., et al., "The Acoustic Cortex in Alzheimer's Disease," Acta Otolaryngol Suppl., vol. 494, 1992, pp. 1-13.
Baloyannis, S.J., "Dendritic Pathology in Alzheimer's Disease," Journal of the Neurological Sciences (2009), doi:10.1016/j.jns.2009.02.370.
De Ruiter, J.P., et al., "Morphometric and Dendritic Analysis of Fascia Dentata Granule Cells in Human Aging and Senile Demetia," Brain Research, 402 (1987) pp. 217-229.
Einstein, G., et al., "Dendritic Pathology of Granule Cells in Alzheimer's Disease is Unrelaed to Neuritic Plaques," The Journal of Neuroscience, vol. 14, No. 8, Aug. 1994, pp. 5077-5088.
Gertz, H.J., et al., "The Septo-Hippocampal Pathway in Patients Suffering from Senile Dementia of Alzheimer's Type. Evidence for Neuronal Plasticity?," Neuroscience Letters, vol. 76, 1987, pp. 228-232.
Hachimi, K.H.E., et al., "Perte des Épines Dendritiques Dans La Maladie d'Alzheimer," Academie des Sciences, Paris, t. 311, Serie III, 1990, pp. 397-402.
Ishida, A., et al., "Protein Phosphatases that Regulate Multifunctional $Ca^{2+}$/ calmodulin-dependent Protein Kinases: From Biochemistry to Pharmacology," Pharmacology & Therapeutics, vol. 100, 2003, pp. 291-305.
Knobloch, M., et al., "Dendritic Spine Loss and Synaptic Alterations in Alzheimer's Disease," Molecular Neurobiology, vol. 37, No. 1, Feb. 2008, pp. 73-82.
Koh, C.-G., et al., "The p21-Activated Kinase PAK is Negatively Regulated by POPX1 and POPX2, a Pair of Serine/Threonine Phosphatases of the PP2C Family," Current Biology, vol. 12, Feb. 2002, pp. 317-321.
Moolman, D.L., et al., "Dendrite and Dendritic Spine Alterations in Alzheimer Models," Journal of Neurocytology, vol. 33, 2004, pp. 377-387.

(Continued)

*Primary Examiner* — Olga N Chernyshev
(74) *Attorney, Agent, or Firm* — Venable LLP; Nancy J. Axelrod; Michael A. Gollin

(57) ABSTRACT

1. Use of
(v) a gene coding for a protein phosphatase 1 E having SEQ ID NO:1 or SEQ ID NO:2, and/or
(vi) a transcription product of the gene coding for a protein phosphatase 1 E having SEQ ID NO:1 or SEQ ID NO:2, and/or
(vii) a translation product of the gene coding for a protein phosphatase 1 E having SEQ ID NO:1 or SEQ ID NO:2, and/or
(viii) a fragment, or derivative, or variant of (i) to (iii).

for identifying or for testing agents for the treatment and/or prevention of neurodegenerative diseases.

3 Claims, 17 Drawing Sheets

(56) References Cited

PUBLICATIONS

Selkoe, D.J., "Alzheimer's Disease is a Synaptic Failure," Science, vol. 298, Oct. 2002, pp. 789-791.

Spires, T.L., et al., "Dendritic Spine Abnormalities in Amyloid Precursor Protein Transgenic Mice Demonstrated by Gene Transfer and Intravital Multiphoton Microscopy," The Journal of Neuroscience, vol. 25, No. 31, Aug. 2005, pp. 7278-7287.

Tackenberg, C., et al., "Thin, Stubby or Mushroom: Spine Pathology in Alzheimer's Disease," Current Alzheimer Research, vol. 6, 2009, pp. 261-268.

Takeuchi, M., et al., "Identification and Characterization of Nuclear Localization Signals of CaMKP-N," Journal of Biochemistry, vol. 136, 2004, pp. 183-188.

Terry, R.D., et al., "Physical Basis of Cognitive Alterations in Alzheimer's Disease: Synapse Loss is the Major Correlate of Cognitive Impairment," Annals of Neurology, vol. 30, 1991, 572-580.

measured data of PPM1E mRNA expression in frontal and inferior temporal cortices in Braak stages 0 – 4

| Donor | Braak stage | PPM1E F | PPM1E T |
|---|---|---|---|
| C011 | 0 | 9,4984 | 11,1779 |
| C012 | 0 | 12,0334 | 6,8716 |
| C026 | 0 | 10,3981 | 11,4102 |
| C027 | 0 | 1,7605 | 2,9738 |
| C032 | 0 | 12,4562 | 9,4556 |
| C014 | 1 | 28,4737 | 24,1058 |
| C028 | 1 | 26,2280 | 19,4305 |
| C029 | 1 | 46,4650 | 27,7498 |
| C030 | 1 | 7,3337 | 11,0323 |
| C036 | 1 | 10,4086 | 6,4433 |
| C038 | 1 | 3,7701 | 4,1549 |
| C039 | 1 | 9,2583 | 10,9901 |
| C008 | 2 | 64,6831 | 48,1217 |
| C031 | 2 | 28,3925 | 21,7860 |
| C033 | 2 | 42,5926 | 19,8108 |
| C034 | 2 | 29,8759 | 18,8695 |
| DE03 | 2 | 18,0693 | 26,2374 |
| C025 | 3 | 43,7298 | 15,4799 |
| DE07 | 3 | 20,7970 | 24,0498 |
| DE11 | 3 | 17,6282 | 25,2891 |
| C057 | 3 | 17,0949 | 39,5389 |
| P012 | 4 | 14,0607 | 19,0353 |
| P047 | 4 | 12,8040 | 38,4146 |
| P068 | 4 | 4,7350 | 8,4175 |

Fig.1A

Length: 755 aa

```
  1  MAGCIPEEKT  YRRFLELFLG  EFRGPCGGGE  PEPEPEPEPE  PEPESEPEPE
 51  PELVEAEAAE  ASVEEPGEEA  ATVAATEEGD  QEQDPEPEEE  AAVEGEEEEE
101  GAATAAAAPG  HSAVPPPPPQ  LPPLPPLPRP  LSERITREEV  EGESLDLCLQ
151  QLYKYNCPSF  LAAALARATS  DEVLQSDLSA  HYIPKETDGT  EGTVEIETVK
201  LARSVFSKLH  EICCSWVKDF  PLRRRPQLYY  ETSIHAIKNM  RRKMEDKHVC
251  IPDFNMLFNL  EDQEEQAYFA  VFDGHGGVDA  AIYASIHLHV  NLVRQEMFPH
301  DPAEALCRAF  RVTDERFVQK  AARESLRCGT  TGVVTFIRGN  MLHVAWVGDS
351  QVMLVRKGQA  VELMKPHKPD  REDEKQRIEA  LGGCVVWFGA  WRVNGSLSVS
401  RAIGDAEHKP  YICGDADSAS  TVLDGTEDYL  ILACDGFYDT  VNPDEAVKVV
451  SDHLKENNGD  SSMVAHKLVA  SARDAGSSDN  ITVIVVFLRD  MNKAVNVSEE
501  SDWTENSFQG  GQEDGGDDKE  NHGECKRPWP  QHQCSAPADL  GYDGRVDSFT
551  DRTSLSPGSQ  INVLEDPGYL  DLTQIEASKP  HSAQFLLPVE  MFGPGAPKKA
601  NLINELMMEK  KSVQSSLPEW  SGAGEFPTAF  NLGSTGEQIY  RMQSLSPVCS
651  GLENEQFKSP  GNRVSRLSHL  RHHYSKKWHR  FRFNPKFYSF  LSAQEPSHKI
701  GTSLSSLTGS  GKRNRIRSSL  PWRQNSWKGY  SENMRKLRKT  HDIPCPDLPW
751  SYKIE
```

Fig. 3A

Length: 557 aa

```
  1  MAGCIPEEKT  YRRFLELFLG  EFRGPCGGGE  PEPEPEPEPE  PEPESEPEPE
 51  PELVEAEAAE  ASVEEPGEEA  ATVAATEEGD  QEQDPEPEEE  AAVEGEEEEE
101  GAATAAAAPG  HSAVPPPPPQ  LPPLPPLPRP  LSERITREEV  EGESLDLCLQ
151  QLYKYNCPSF  LAAALARATS  DEVLQSDLSA  HYIPKETDGT  EGTVEIETVK
201  LARSVFSKLH  EICCSWVKDF  PLRRRPQLYY  ETSIHAIKNM  RRKMEDKHVC
251  IPDFNMLFNL  EDQEEQAYFA  VFDGHGGVDA  AIYASIHLHV  NLVRQEMFPH
301  DPAEALCRAF  RVTDERFVQK  AARESLRCGT  TGVVTFIRGN  MLHVAWVGDS
351  QVMLVRKGQA  VELMKPHKPD  REDEKQRIEA  LGGCVVWFGA  WRVNGSLSVS
401  RAIGDAEHKP  YICGDADSAS  TVLDGTEDYL  ILACDGFYDT  VNPDEAVKVV
451  SDHLKENNGD  SSMVAHKLVA  SARDAGSSDN  ITVIVVFLRD  MNKAVNVSEE
501  SDWTENSFQG  GQEDGGDDKE  NHGECKRPWP  QHQCSAPADL  GYDGRVDSFT
551  DRTSLSP
```

```
   1  TGCTGATCGC TCGTGCCGGT GCGGCCGTTA ACCGCCCTTG CCGGAGCCCT
  51  AGGCTCAAAA GCAGCCCCTT ACCCTTCCTG GGCTTCCCCC AACCCCTTTC
 101  CCGGTCTGCC CTGGGGCATG AGCAGCGATG GCCGGCTGCA TCCCTGAGGA
 151  GAAAACTTAC CGGCGCTTCC TGGAGCTATT CCTGGGCGAG TTTCGCGGAC
 201  CGTGCGGCGG CGGCGAGCCG GAGCCGGAAC CCGAACCCGA ACCCGAACCC
 251  GAACCCGAGT CCGAGCCCGA GCCCGAACCT GAACTGGTAG AAGCTGAGGC
 301  GGCCGAGGCT TCGGTAGAGG AACCCGGGGA GGAGGCGGCC ACGGTAGCCG
 351  CGACGGAGGA GGGGGACCAG GAGCAAGACC CGGAGCCCGA GGAGGAGGCG
 401  GCGGTTGAGG GTGAGGAGGA GGAGGAGGGC GCGGCGACGG CGGCGGCAGC
 451  CCCGGGGCAC TCGGCCGTGC CGCCGCCGCC GCCCCAGCTG CCGCCTTTGC
 501  CCCCGCTCCC GCGACCGCTG TCAGAGCGCA TCACCCGCGA GGAGGTGGAG
 551  GGCGAAAGCC TGGACCTGTG CCTGCAGCAG CTCTACAAAT ATAATTGCCC
 601  TTCCTTTTTG GCTGCTGCTT TAGCCAGAGC CACATCAGAT GAAGTCCTTC
 651  AGAGTGATCT TTCTGCACAT TATATCCCAA AGGAAACGGA TGGCACAGAA
 701  GGGACTGTGG AGATTGAGAC AGTGAAATTG GCCCGTTCTG TCTTCAGCAA
 751  ACTACACGAG ATTTGCTGCA GCTGGGTGAA AGACTTCCCC CTCCGCAGGA
 801  GACCCCAGCT TTATTATGAG ACATCAATCC ATGCCATCAA AAACATGCGC
 851  AGGAAAATGG AGGACAAACA TGTCTGCATT CCTGACTTTA ATATGCTCTT
 901  CAACCTAGAG GACCAGGAAG AACAAGCTTA CTTTGCAGTG TTTGATGGCC
 951  ATGGGGGAGT AGATGCTGCT ATTTATGCCT CCATTCACCT CCACGTTAAC
1001  TTAGTCCGCC AGGAGATGTT CCCCCATGAT CCTGCTGAGG CCCTGTGCAG
1051  GGCCTTCCGG GTCACTGATG AGCGGTTTGT GCAGAAAGCA GCCAGGGAGA
1101  GCTTAAGATG TGGGACCACA GGAGTGGTGA CTTTCATCAG AGGCAACATG
1151  CTACATGTGG CCTGGGTGGG TGATTCCCAG GTTATGCTTG TGAGAAAGGG
1201  CCAAGCTGTT GAACTAATGA AGCCACACAA ACCAGACAGA GAGGATGAAA
1251  AGCAGAGAAT TGAGGCCCTT GGAGGTTGCG TAGTCTGGTT TGGTGCCTGG
1301  AGGGTGAATG GAAGTCTGTC GGTTTCCAGA GCTATTGGAG ATGCTGAACA
1351  TAAGCCATAT ATCTGTGGGG ATGCAGATTC TGCCTCCACT GTTCTGGATG
1401  GGACCGAAGA CTACCTCATT CTGGCCTGTG ATGGCTTCTA TGACACCGTG
1451  AACCCTGATG AGGCAGTGAA AGTTGTGTCC GACCACCTGA AAGAGAATAA
1501  TGGAGACAGC AGCATGGTTG CCCACAAATT AGTGGCATCA GCTCGTGATG
1551  CTGGGTCAAG TGATAACATC ACGGTTATTG TGGTATTCCT GAGGGACATG
1601  AACAAAGCTG TAAATGTTAG TGAGGAATCA GATTGGACAG AGAACTCTTT
1651  TCAAGGAGGG CAAGAAGATG GTGGGGATGA TAAGGAGAAT CATGGAGAGT
1701  GCAAACGCCC TTGGCCTCAG CACCAGTGCT CAGCACCAGC CGACCTAGGC
1751  TATGATGGGC GTGTGGATTC ATTCACTGAT AGAACTAGCC TGAGCCCAGG
1801  GTCCCAAATC AACGTGCTGG AAGACCCAGG CTACCTAGAT CTCACACAAA
1851  TAGAAGCAAG CAAACCTCAC AGTGCCCAGT TTTTGCTACC AGTTGAGATG
1901  TTTGGTCCTG GTGCACCAAA GAAAGCAAAT CTTATTAATG AGTTAATGAT
1951  GGAGAAAAAA TCAGTTCAGT CATCATTGCC TGAATGGAGT GGTGCTGGAG
2001  AGTTTCCCAC TGCTTTCAAT TTGGGTTCAA CAGGGGAGCA GATATACAGA
2051  ATGCAGAGCT TGTCTCCTGT CTGTTCAGGG TTGGAAAATG AACAGTTCAA
2101  ATCCCGGGA AACAGAGTTT CTAGATTGTC TCATTTACGC CACCACTACT
2151  CAAAGAAGTG GCACAGATTC AGGTTTAATC CAAAGTTTTA TTCATTTCTC
2201  TCTGCTCAAG AGCCTTCCCA CAAAATAGGC ACTAGCCTGT CCTCACTTAC
2251  TGGAAGTGGG AAGAGAAATA GGATAAGAAG TTCTCTGCCA TGGAGGCAAA
2301  ATAGTTGGAA AGGGTACAGT GAAAACATGA GGAAGCTCAG AAAGACTCAT
2351  GATATTCCAT GCCCAGATCT TCCTTGGAGC TATAAAATAG AATAATTTTT
2401  CTTTCAAGTA GGTTAGCTAG CTCTCCCCCA ATAAAAATAC CACTATCAGA
2451  GTAGAAACAA GGTAGACATT TCTAAAACAT ATGTGCTTCA TTATGAATCC
2501  ATGGATGGCT CAATTCTTAA ATGTAAATAG ATCTCTAGGA AACTCAAAGT
2551  ACAGTGTTTT CAATCTAAAA AGAAGTATTG GCAGTTTCAC TTGCAAAATT
2601  ACACAGCTGG TCCCTGTGAT GTGTCTCGAC ACCAATACAC AACCCCCTTC
2651  CCACCATCCT TCATGTCACT AGATACACAA CCCCCTTCCC ACCATCCCTT
```

FIG. 4 (CON'T)

```
2701  CAGTCACTAG TGGAAGCTTT CAAGTTAGTT ATTTCAGTCA GGATATACAG
2751  TGTTGAAATC TCAATGCAGT TGAAATCTGG TCTGATGTGC CTAATTTATC
2801  TGTGGAAAAT TTAATGCTGA ATTACATTTG GTTGGGAAAT GTCCCTCAAA
2851  ATCCTGGGCA CTATGAAGGA ACCCCCTGCC CCCTCACCTT TTTGGGTAGG
2901  TAAAAGACTA AAAGCCATAT GGATTTTAAC TGATAACAAT GAAAGTGGTA
2951  AATCAGTGTA AAAGTGTCAT ATTCTCAGAC TTGTGAGGCG GTTTATAGTC
3001  AGAAAGATTT ACGGATTTTT TTCCTGTAAC ATAAAAGATT GTGAACTTTT
3051  TTTAATTAAA AAATATTTCC TAGGGCTGTA GTTATTGGG AGTTTCATAA
3101  CCTGTTATGG TGCTTTTGGT GGAAATTTTT ATTATTTAGC ATTTTAGGAG
3151  ACCGCTGTCA ACTGGTTTTA ATCTATGATG CTAATGTGTT TTCCACTGTA
3201  CCCTCATCTC AGGAATAAAA CTGCTTTAAC GGAGATGATG TCAGGTACAA
3251  ATACACTATA GAGTCAAAAT ACCATTTACA AAGAAAATCA AAAGCATTTC
3301  TATATTTTGT CTTTTTTTAG TTCAGACAGC AAAGGCATGT ACTACTATAA
3351  AATACAAAGT GATTTTAGAG AATGAAAAAT GCTACTTTTA TCTTCTCTAA
3401  AATTATTTCC CCCAAGGTAG TGAAGTAATT GGAATGAAGG AGGCTGAAAG
3451  TATTGTCTAA AGTGAGCCCA GAGGCCACTG AGAATGCAGA TTACTGACAG
3501  CCAGGTCTGT TTAGTTGTAA TTGGAAGACA CATGAGTGTC CTGCTTACAT
3551  GTAGCTTCAG ACTGCAGAGA CAGGACGTGT GCTTTTCATT TCAATATTTA
3601  GTTATATTTG ATATTTTGAA ACTGTCTGCT TTTTGCTATT TCTGCAGTTT
3651  CAAGTTAGTT AGAAGCATGT TGTCAACTAA AGACAACAAA CTATCAGATT
3701  CATTCATTCA GTGAAGCAGC CTCTGATTCT CTAAGAGTCA CGAATGTCTT
3751  AGTGTTACCC TCCCCTAGTC AACAGCAGAC CAGCCTGGCC AATGCCTATG
3801  GGTGGCCCCT CTGGAGTGCT CACTAACAAG GGTGAGTGCT CTCGCTAAGA
3851  AGTGTCCCCC GCCTAATCAT GTGTTTATAG GATAGTACAC GTTCCCCAGG
3901  CCCATAACAG AGGACTAAAA TCTCTGAATT TTAAAGACAC AGATGACTGG
3951  CATATTTTGG ATACCAGTAT AGCTATATCA AATAGACAAA AACAGCTTCA
4001  CTTTAGCAAT GATCAGATTG TTAATCTACA GATTTTATTT TTTAAAATTT
4051  GGATGTAAGT AGAGACTTTC AGTATTTGTT TTCTCTTGAT TTTGAAGTCA
4101  TTTCTTCTTC TCACGTCTGT GACAAATGGT TGAAAAGGAG TCAACATGGC
4151  CCCAACTATA GTGCCGGAAC CTTTTCATCA TTCTGAGGCT TTGCCCCACA
4201  CATGGTCCTC ACTCATATCT GTCACCTTCT GAAGCCTAGA TCTTGTTAAC
4251  CCATCAGGTG CAGTGTCAGT TTCAAATCAA ATTATCTAAG AAAACAAGAA
4301  AACAAAGGCA GCAGACTATT GGTACACATT ATAGTCCAAA GTGCTTAGCG
4351  AAGTAAAAAA AAAAGCTTTT TAAAATTTCT ATTGTTGTCT ATTGGTAATG
4401  TTTTTGATCA GAATAAAGAG GGTAAAGGGA AAAAGTTACT ACACATGCTA
4451  GGCTTTCTCA GTGGGAAAA AAATGGCTGG ATAGAACTGG GACAAACACA
4501  GACCCATCTT TAGGGGTCTG GATTTTGTAG GTCCGACTAC ACAGCAGTGT
4551  TAACTCATTT CTCATGCCAT TAGCTCTCTA CAAAATAAAG CAAAGTAGTT
4601  CTAGTGTGGT CGTTATAAAC CAATATTGTG AAAAATAGCA ACTATTCATT
4651  TGTTCACAAC ATGCGTATTT ATAGAGTAGT TAGGTACCAT TTGTAAGGTA
4701  AATCCTTTAA AATTCTATAA TACATACTAA AATAGTGGTT ATTGGTCTGA
4751  TATATGCTGC TCTTGGTTCT ATAAACTAGA TAAAAGCAGT GCTTTGTGAA
4801  ATGCAGTGTT CTCTCTTAAC GCCACTGGTG ATAGGAAGTA GTTCCCTTCA
4851  GTTCAAATCC TGTGCCCTTA TTTGCTGCTT GCTGACGTAA GCAATAAGTA
4901  ACCCTCTAAC TAATGGTATC TACATATTTC TGTAACTTGT ATTTAATGAT
4951  GGTGTACCTG GTGATTGTAA AAATATTAGA CAGATATAAA AGTATCTATA
5001  TAATATCTAT AAACTGTTAA TGCTGAGGTA TAGTCTGTGA ATTATGTGTT
5051  TTGTATTTTT ATTCATTGTG TAATTTAGTG GTGGTGAAAG TTCTACACTC
5101  AATCCTTAAA GAGTGGCAGT ATCCCTTTTT CAATTTAACA TGGTCTGCAT
5151  CAATCTGTTT GCCTGCTAAA CAAGTTAGAA TAGGAAATAG TAAAATAAAT
5201  CCAAACAAGA GTGTAATATT GGTTAGGGAA ACAAACTTCA GGTCACCAAC
5251  TGAAGTCATT ACAAACTCCT TGTACATTCA CTGTGAGTTT CAAAGGGAGT
5301  CAGTCCCTAA TTTACAGGTT TCCTTTGTTC ACTTCTAGA TGTGTACTTT
5351  TGAGGGACAT GAGGTTAGGC AACATTACAG CAACACACAC TGGGGCTATT
5401  AATCCCATTT AGGTCTGTAC TAAAGAGGAT GGGTAGAAAC ACATATGTAT
```

FIG. 4 (CON'T)

```
5451  ATACCTTTTC TTTACCTAGA AGTGCCATCC ATTGTCCTTG AATTATTATG
5501  ATTAAAGTTA CTGTTGCATT TAGGAGGCTC CTTGAAAGTA ACACCTTTTC
5551  CAAGGACAAT GGCAACAATG TCAATGTCAA CACTGAGTCT AATTTTGACC
5601  ACATTTATAG TGGTATAGTG TCAATACTGC ATTTTCATGA CAACCACACT
5651  CCACTGTTGA AACACTGTGC CAGTGAGAAG TGCAACATCC AGTGGGCAGA
5701  TGAAAATGAT GCATGGCCAA GTTCAGTGTT TACAGATAAA ACTGCTGTGG
5751  TTCAAGTGCT TCCTTCCCCA TCAAATCCTT GATAAGGCTT TGTGGGAAAA
5801  TGATCTAAAT TATTGTTTTA ATTTTTAAAC CTAATTTATT CACTCAGTGA
5851  ACATTCTTAC CTAAGCAAGG CTATAAAAGG GAATACTACA GTTTTGTCCA
5901  CACTTTAATT TGAGACCATT TTTCTTTGAA TCGTAAGTTA GCAAAAGAAA
5951  TTTTTTTCAC CTTTGAAAAT CACGTGATGT TAAAGGACAA ATGCCCACTC
6001  TTCTATTCTG ATCTGCAAAT AGCTTAAATG TCTCTTGCAA AACAAAGTAA
6051  GATACCACCA GTATTACAAC ACAATGATTT TCCAGACAAA TGGTATGGTG
6101  TTGAAAAATA ACTGTTACTT CTTAAAGCAG CATTTTATCT TCTATTTTGA
6151  AGACTATTTA TTGTAATAAT TAGAAAACAT GAAATAGGGA ACTCCAGACT
6201  GACACAGCAG TTGTTTTTGA AAAGGAAATA AACTTTGATG AATTAGATAA
6251  TCCAGATACA TCATTGTAAA CTCTTACTCT AGGTGCTCTT TGGTGAGAGA
6301  CAGGCTTGT  TCTCTTGTTC ATAACATTTC TCTGCAAAGA ATTCTCTATG
6351  GAGTGAAGCG AATGAAGTGA ATAATTTCTT ACCAAATAAA TTTATCAATT
6401  TACAAATCTG CTCTACATCT CACTTTTGAG TTCAGTTGTA GTCATGAGTG
6451  ATCCTTCATA TTTTATTAAA AGTGTTCATT CAGGTAAGGT GTATGTTGAA
6501  ATTTTGCCAA TTATCTTAAT AAAACCTGGC AATTT
```

Fig.5

Length: 2268 bp

```
   1  atggccggct gcatccctga ggagaaaact taccggcgct tcctggagct
  51  attcctgggc gagtttcgcg gaccgtgcgg cggcggcgag ccggagccgg
 101  aacccgaacc cgaacccgaa cccgaacccg agtccgagcc cgagcccgaa
 151  cctgaactgg tagaagctga ggcggccgag gcttcggtag aggaacccgg
 201  ggaggaggcg gccacggtag ccgcgacgga ggaggggggac caggagcaag
 251  acccggagcc cgaggaggag gcggcggttg agggtgagga ggaggaggag
 301  ggcgcggcga cggcggcggc agccccgggg cactcggccg tgccgccgcc
 351  gccgccccag ctgccgcctt tgccccgct cccgcgaccg ctgtcagagc
 401  gcatcacccg cgaggaggtg gagggcgaaa gcctggacct gtgcctgcag
 451  cagctctaca aatataattg cccttccttt ttggctgctg ctttagccag
 501  agccacatca gatgaagtcc ttcagagtga tctttctgca cattatatcc
 551  caaaggaaac ggatggcaca gagggactg tggagattga gacagtgaaa
 601  ttggcccgtt ctgtcttcag caaactacac gagatttgct gcagctgggt
 651  gaaagacttc ccctccgca ggaga cccca gctttattat gagacatcaa
 701  tccatgccat caaaaacatg cgcaggaaaa tggaggacaa acatgtctgc
 751  attcctgact ttaatatgct cttcaaccta gaggaccagg aagaacaagc
 801  ttactttgca gtgtttgatg gccatggggg agtagatgct gctatttatg
 851  cctccattca cctccacgtt aacttagtcc gccaggagat gttcccccat
 901  gatcctgctg aggccctgtg cagggccttc cgggtcactg atgagcggtt
 951  tgtgcagaaa gcagccaggg agagcttaag atgtgggacc acaggagtgg
1001  tgactttcat cagaggcaac atgctacatg tggcctgggt gggtgattcc
1051  caggttatgc ttgtgagaaa gggccaagct gttgaactaa tgaagccaca
1101  caaaccagac agagaggatg aaaagcagag aattgaggcc cttggaggtt
1151  gcgtagtctg gtttggtgcc tggagggtga atggaagtct gtcggtttcc
1201  agagctattg gagatgctga acataagcca tatatctgtg gggatgcaga
1251  ttctgcctcc actgttctgg atgggaccga agactacctc attctggcct
1301  gtgatggctt ctatgacacc gtgaaccctg atgaggcagt gaaagttgtg
1351  tccgaccacc tgaaagagaa taatggagac agcagcatgg ttgcccacaa
1401  attagtggca tcagctcgtg atgctgggtc aagtgataac atcacggtta
1451  ttgtggtatt cctgagggac atgaacaaag ctgtaaatgt tagtgaggaa
1501  tcagattgga cagagaactc ttttcaagga gggcaagaag atggtgggga
1551  tgataaggag aatcatggag agtgcaaacg cccttggcct cagcaccagt
1601  gctcagcacc agccgaccta ggctatgatg ggcgtgtgga ttcattcact
1651  gatagaacta gcctgagccc agggtcccaa atcaacgtgc tggaagaccc
1701  aggctaccta gatctcacac aaatagaagc aagcaaacct cacagtgccc
1751  agttttgct accagttgag atgtttggtc ctggtgcacc aaagaaagca
1801  aatcttatta atgagttaat gatggagaaa aaatcagttc agtcatcatt
1851  gcctgaatgg agtggtgctg gagagtttcc cactgctttc aatttgggtt
1901  caacagggga gcagatatac agaatgcaga gcttgtctcc tgtctgttca
1951  gggttggaaa atgaacagtt caaatccccg ggaaacagag tttctagatt
2001  gtctcattta cgccaccact actcaaagaa gtggcacaga ttcaggttta
2051  atccaaagtt ttattcattt ctctctgctc aagagccttc ccacaaaata
2101  ggcactagcc tgtcctcact tactggaagt gggaagagaa ataggataag
2151  aagttctctg ccatggaggc aaaatagttg gaaagggtac agtgaaaaca
2201  tgaggaagct cagaaagact catgatattc catgcccaga tcttccttgg
2251  agctataaaa tagaataa
```

SEQ ID NO:5 (PRIMER A)      1 GTTCTGGATGGGACCGAAGA   20
                              ||||||||||||||||||||
SEQ ID NO:4              1264 GTTCTGGATGGGACCGAAGA 1283

SEQ ID NO:6 (PRIMER B)     21 AAAGTTGTGTCCGACCACCTG  1
                              |||||||||||||||||||||
SEQ ID NO:4              1342 AAAGTTGTGTCCGACCACCTG 1362

Fig. 13
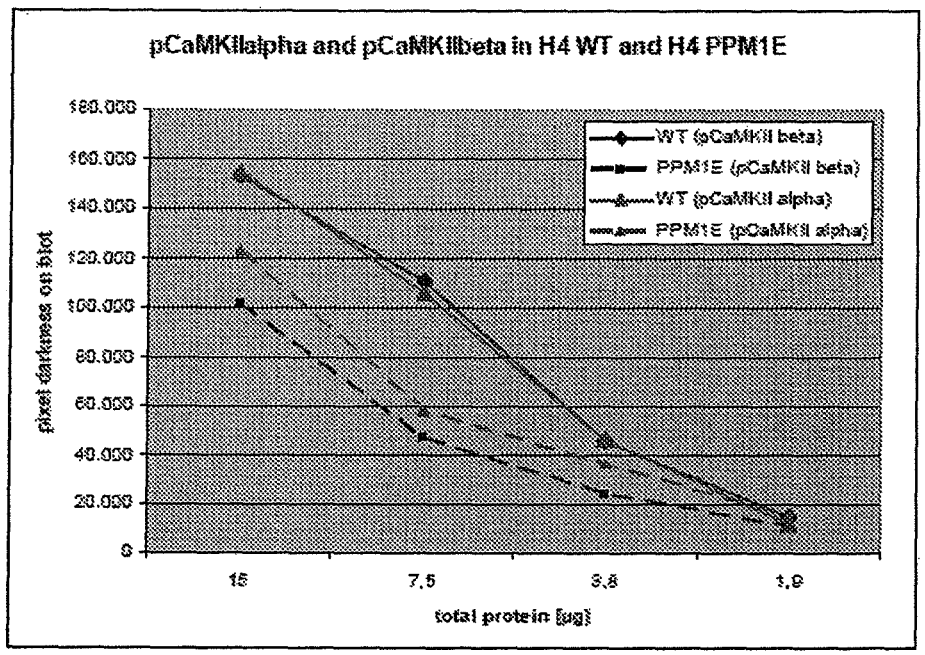
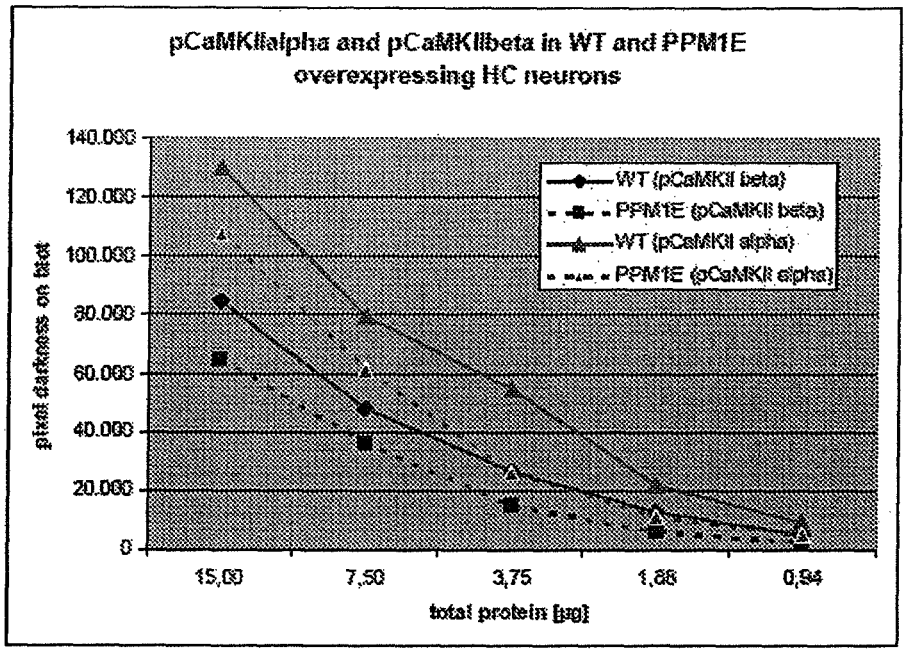

P-value = 0.061, Student's T-test

SEQUENCE LISTING

<160> NUMBER OF SEQ ID NOS: 8

<210> SEQ ID NO 1
<211> LENGTH: 755
<212> TYPE: PRT
<213> ORGANISM: Homo sapiens

<400> SEQUENCE: 1

```
Met Ala Gly Cys Ile Pro Glu Glu Lys Thr Tyr Arg Arg Phe Leu Glu
1               5                   10                  15

Leu Phe Leu Gly Glu Phe Arg Gly Pro Cys Gly Gly Gly Glu Pro Glu
            20                  25                  30

Pro Glu Pro Glu Pro Glu Pro Glu Pro Glu Pro Ser Glu Pro Glu
        35                  40                  45

Pro Glu Pro Glu Leu Val Glu Ala Glu Ala Glu Ala Ser Val Glu
    50                  55                  60

Glu Pro Gly Glu Ala Ala Thr Val Ala Ala Thr Glu Glu Gly Asp
65                  70                  75                  80

Gln Glu Gln Asp Pro Glu Pro Glu Glu Ala Val Glu Gly Glu
            85                  90                  95

Glu Glu Glu Glu Gly Ala Ala Thr Ala Ala Ala Pro Gly His Ser
            100                 105                 110

Ala Val Pro Pro Pro Pro Gln Leu Pro Pro Leu Pro Pro Leu Pro
            115                 120                 125

Arg Pro Leu Ser Glu Arg Ile Thr Arg Glu Glu Val Glu Gly Glu Ser
    130                 135                 140

Leu Asp Leu Cys Leu Gln Gln Leu Tyr Lys Tyr Asn Cys Pro Ser Phe
145                 150                 155                 160

Leu Ala Ala Ala Leu Ala Arg Ala Thr Ser Asp Glu Val Leu Gln Ser
                    165                 170                 175

Asp Leu Ser Ala His Tyr Ile Pro Lys Glu Thr Asp Gly Thr Glu Gly
                180                 185                 190

Thr Val Glu Ile Glu Thr Val Lys Leu Ala Arg Ser Val Phe Ser Lys
            195                 200                 205

Leu His Glu Ile Cys Cys Ser Trp Val Lys Asp Phe Pro Leu Arg Arg
    210                 215                 220

Arg Pro Gln Leu Tyr Tyr Glu Thr Ser Ile His Ala Ile Lys Asn Met
225                 230                 235                 240

Arg Arg Lys Met Glu Asp Lys His Val Cys Ile Pro Asp Phe Asn Met
                    245                 250                 255

Leu Phe Asn Leu Glu Asp Gln Glu Glu Gln Ala Tyr Phe Ala Val Phe
                260                 265                 270

Asp Gly His Gly Gly Val Asp Ala Ala Ile Tyr Ala Ser Ile His Leu
            275                 280                 285

His Val Asn Leu Val Arg Gln Glu Met Phe Pro His Asp Pro Ala Glu
    290                 295                 300
```

```
Ala Leu Cys Arg Ala Phe Arg Val Thr Asp Glu Arg Phe Val Gln Lys
305                 310                 315                 320

Ala Ala Arg Glu Ser Leu Arg Cys Gly Thr Thr Gly Val Val Thr Phe
            325                 330                 335

Ile Arg Gly Asn Met Leu His Val Ala Trp Val Gly Asp Ser Gln Val
            340                 345                 350

Met Leu Val Arg Lys Gly Gln Ala Val Glu Leu Met Lys Pro His Lys
            355                 360                 365

Pro Asp Arg Glu Asp Glu Lys Gln Arg Ile Glu Ala Leu Gly Gly Cys
        370                 375                 380

Val Val Trp Phe Gly Ala Trp Arg Val Asn Gly Ser Leu Ser Val Ser
385                 390                 395                 400

Arg Ala Ile Gly Asp Ala Glu His Lys Pro Tyr Ile Cys Gly Asp Ala
                405                 410                 415

Asp Ser Ala Ser Thr Val Leu Asp Gly Thr Glu Asp Tyr Leu Ile Leu
            420                 425                 430

Ala Cys Asp Gly Phe Tyr Asp Thr Val Asn Pro Asp Glu Ala Val Lys
        435                 440                 445

Val Val Ser Asp His Leu Lys Glu Asn Asn Gly Asp Ser Ser Met Val
450                 455                 460

Ala His Lys Leu Val Ala Ser Ala Arg Asp Ala Gly Ser Ser Asp Asn
465                 470                 475                 480

Ile Thr Val Ile Val Phe Leu Arg Asp Met Asn Lys Ala Val Asn
                485                 490                 495

Val Ser Glu Glu Ser Asp Trp Thr Glu Asn Ser Phe Gln Gly Gly Gln
            500                 505                 510

Glu Asp Gly Gly Asp Asp Lys Glu Asn His Gly Glu Cys Lys Arg Pro
            515                 520                 525

Trp Pro Gln His Gln Cys Ser Ala Pro Ala Asp Leu Gly Tyr Asp Gly
        530                 535                 540

Arg Val Asp Ser Phe Thr Asp Arg Thr Ser Leu Ser Pro Gly Ser Gln
545                 550                 555                 560

Ile Asn Val Leu Glu Asp Pro Gly Tyr Leu Asp Leu Thr Gln Ile Glu
                565                 570                 575

Ala Ser Lys Pro His Ser Ala Gln Phe Leu Leu Pro Val Glu Met Phe
            580                 585                 590

Gly Pro Gly Ala Pro Lys Lys Ala Asn Leu Ile Asn Glu Leu Met Met
            595                 600                 605

Glu Lys Lys Ser Val Gln Ser Ser Leu Pro Glu Trp Ser Gly Ala Gly
        610                 615                 620

Glu Phe Pro Thr Ala Phe Asn Leu Gly Ser Thr Gly Glu Gln Ile Tyr
625                 630                 635                 640

Arg Met Gln Ser Leu Ser Pro Val Cys Ser Gly Leu Glu Asn Glu Gln
                645                 650                 655

Phe Lys Ser Pro Gly Asn Arg Val Ser Arg Leu Ser His Leu Arg His
            660                 665                 670

His Tyr Ser Lys Lys Trp His Arg Phe Arg Phe Asn Pro Lys Phe Tyr
            675                 680                 685

Ser Phe Leu Ser Ala Gln Glu Pro Ser His Lys Ile Gly Thr Ser Leu
        690                 695                 700

Ser Ser Leu Thr Gly Ser Gly Lys Arg Asn Arg Ile Arg Ser Ser Leu
705                 710                 715                 720

Pro Trp Arg Gln Asn Ser Trp Lys Gly Tyr Ser Glu Asn Met Arg Lys
```

```
                        725                 730                 735
Leu Arg Lys Thr His Asp Ile Pro Cys Pro Asp Leu Pro Trp Ser Tyr
        740                 745                 750

Lys Ile Glu
        755

<210> SEQ ID NO 2
<211> LENGTH: 557
<212> TYPE: PRT
<213> ORGANISM: Homo sapiens

<400> SEQUENCE: 2

Met Ala Gly Cys Ile Pro Glu Glu Lys Thr Tyr Arg Arg Phe Leu Glu
1               5                   10                  15

Leu Phe Leu Gly Glu Phe Arg Gly Pro Cys Gly Gly Gly Glu Pro Glu
            20                  25                  30

Pro Glu Pro Glu Pro Glu Pro Glu Pro Glu Ser Glu Pro Glu
        35                  40                  45

Pro Glu Pro Glu Leu Val Glu Ala Glu Ala Glu Ala Ser Val Glu
    50                  55                  60

Glu Pro Gly Glu Glu Ala Ala Thr Val Ala Ala Thr Glu Glu Gly Asp
65                  70                  75                  80

Gln Glu Gln Asp Pro Glu Pro Glu Glu Ala Ala Val Glu Gly Glu
                85                  90                  95

Glu Glu Glu Glu Gly Ala Ala Thr Ala Ala Ala Pro Gly His Ser
            100                 105                 110

Ala Val Pro Pro Pro Pro Gln Leu Pro Pro Leu Pro Leu Pro
        115                 120                 125

Arg Pro Leu Ser Glu Arg Ile Thr Arg Glu Glu Val Glu Gly Glu Ser
            130                 135                 140

Leu Asp Leu Cys Leu Gln Gln Leu Tyr Lys Tyr Asn Cys Pro Ser Phe
145                 150                 155                 160

Leu Ala Ala Ala Leu Ala Arg Ala Thr Ser Asp Glu Val Leu Gln Ser
                165                 170                 175

Asp Leu Ser Ala His Tyr Ile Pro Lys Glu Thr Asp Gly Thr Glu Gly
            180                 185                 190

Thr Val Glu Ile Glu Thr Val Lys Leu Ala Arg Ser Val Phe Ser Lys
        195                 200                 205

Leu His Glu Ile Cys Cys Ser Trp Val Lys Asp Phe Pro Leu Arg Arg
    210                 215                 220

Arg Pro Gln Leu Tyr Tyr Glu Thr Ser Ile His Ala Ile Lys Asn Met
225                 230                 235                 240

Arg Arg Lys Met Glu Asp Lys His Val Cys Ile Pro Asp Phe Asn Met
                245                 250                 255

Leu Phe Asn Leu Glu Asp Gln Glu Gln Ala Tyr Phe Ala Val Phe
            260                 265                 270

Asp Gly His Gly Gly Val Asp Ala Ala Ile Tyr Ala Ser Ile His Leu
        275                 280                 285

His Val Asn Leu Val Arg Gln Glu Met Phe Pro His Asp Pro Ala Glu
    290                 295                 300

Ala Leu Cys Arg Ala Phe Arg Val Thr Asp Glu Arg Phe Val Gln Lys
305                 310                 315                 320

Ala Ala Arg Glu Ser Leu Arg Cys Gly Thr Thr Gly Val Val Thr Phe
                325                 330                 335

Ile Arg Gly Asn Met Leu His Val Ala Trp Val Gly Asp Ser Gln Val
```

```
                340             345             350
Met Leu Val Arg Lys Gly Gln Ala Val Glu Leu Met Lys Pro His Lys
            355                 360                 365

Pro Asp Arg Glu Asp Glu Lys Gln Arg Ile Glu Ala Leu Gly Gly Cys
        370                 375                 380

Val Val Trp Phe Gly Ala Trp Arg Val Asn Gly Ser Leu Ser Val Ser
385                 390                 395                 400

Arg Ala Ile Gly Asp Ala Glu His Lys Pro Tyr Ile Cys Gly Asp Ala
                405                 410                 415

Asp Ser Ala Ser Thr Val Leu Asp Gly Thr Glu Asp Tyr Leu Ile Leu
            420                 425                 430

Ala Cys Asp Gly Phe Tyr Asp Thr Val Asn Pro Asp Glu Ala Val Lys
            435                 440                 445

Val Val Ser Asp His Leu Lys Glu Asn Asn Gly Asp Ser Ser Met Val
        450                 455                 460

Ala His Lys Leu Val Ala Ser Ala Arg Asp Ala Gly Ser Ser Asp Asn
465                 470                 475                 480

Ile Thr Val Ile Val Phe Leu Arg Asp Met Asn Lys Ala Val Asn
                485                 490                 495

Val Ser Glu Glu Ser Asp Trp Thr Glu Asn Ser Phe Gln Gly Gly Gln
            500                 505                 510

Glu Asp Gly Gly Asp Asp Lys Glu Asn His Gly Glu Cys Lys Arg Pro
            515                 520                 525

Trp Pro Gln His Gln Cys Ser Ala Pro Ala Asp Leu Gly Tyr Asp Gly
            530                 535                 540

Arg Val Asp Ser Phe Thr Asp Arg Thr Ser Leu Ser Pro
545                 550                 555

<210> SEQ ID NO 3
<211> LENGTH: 6535
<212> TYPE: DNA
<213> ORGANISM: Homo sapiens

<400> SEQUENCE: 3
tgctgatcgc tcgtgccggt gcggccgtta accgcccttg ccggagccct aggctcaaaa    60
gcagcccctt acccttcctg ggcttccccc aaccccttc ccggtctgcc ctggggcatg   120
agcagcgatg gccggctgca tccctgagga gaaaacttac cggcgcttcc tggagctatt   180
cctgggcgag tttcgcggac cgtgcggcgg cggcgagccg gagccggaac ccgaacccga   240
acccgaaccc gaacccgagt ccgagcccga gcccgaacct gaactggtag aagctgaggc   300
ggccgaggct tcggtagagg aacccgggga ggaggcggcc acggtagccg cgacggagga   360
gggggaccag gagcaagacc cggagcccga ggaggaggcg gcggttgagg gtgaggagga   420
ggaggagggc gcggcgacgg cggcggcagc cccgggcac tcggccgtgc cgccgccgcc   480
gccccagctg ccgcctttgc ccccgctccc gcgaccgctg tcagagcgca tcacccgcga   540
ggaggtggag ggcgaaagcc tggacctgtg cctgcagcag ctctacaaat ataattgccc   600 ttccttttg gctgctgctt tagccagagc cacatcagat gaagtccttc agagtgatct   660
ttctgcacat tatatcccaa aggaaacgga tggcacagaa gggactgtgg agattgagac   720
agtgaaattg gcccgttctg tcttcagcaa actacacga atttgctgca gctgggtgaa   780
agacttcccc ctccgcagga ccccagct ttattatgag acatcaatcc atgccatcaa   840
aaacatgcgc aggaaaatgg aggacaaaca tgtctgcatt cctgacttta atatgctctt   900
caacctagag gaccaggaag aacaagctta ctttgcagtg tttgatggcc atgggggagt   960
```

```
agatgctgct atttatgcct ccattcacct ccacgttaac ttagtccgcc aggagatgtt    1020
cccccatgat cctgctgagg ccctgtgcag ggccttccgg gtcactgatg agcggtttgt    1080
gcagaaagca gccagggaga gcttaagatg tgggaccaca ggagtggtga ctttcatcag    1140
aggcaacatg ctacatgtgg cctgggtggg tgattcccag gttatgcttg tgagaaaggg    1200
ccaagctgtt gaactaatga agccacacaa accagacaga gaggatgaaa agcagagaat    1260
tgaggccctt ggaggttgcg tagtctggtt tggtgcctgg agggtgaatg gaagtctgtc    1320
ggtttccaga gctattggag atgctgaaca taagccatat atctgtgggg atgcagattc    1380
tgcctccact gttctggatg ggaccgaaga ctacctcatt ctggcctgtg atggcttcta    1440
tgacaccgtg aaccctgatg aggcagtgaa agttgtgtcc gaccacctga agagaataa    1500 tggagacagc agcatggttg cccacaaatt agtggcatca gctcgtgatg ctgggtcaag    1560
tgataacatc acggttattg tggtattcct gagggacatg aacaaagctg taatgttag    1620 tgaggaatca gattggacag agaactcttt tcaaggaggg caagaagatg gtggggatga    1680
taaggagaat catggagagt gcaaacgccc ttggcctcag caccagtgct cagcaccagc    1740
cgacctaggc tatgatgggc gtgtggattc attcactgat agaactagcc tgagcccagg    1800
gtcccaaatc aacgtgctgg aagacccagg ctacctagat ctcacacaaa tagaagcaag    1860
caaacctcac agtgcccagt ttttgctacc agttgagatg tttggtcctg gtgcaccaaa    1920
gaaagcaaat cttattaatg agttaatgat ggagaaaaaa tcagttcagt catcattgcc    1980
tgaatggagt ggtgctggag agtttcccac tgctttcaat ttgggttcaa caggggagca    2040
gatatacaga atgcagagct tgtctcctgt ctgttcaggg ttggaaaatg aacagttcaa    2100
atccccggga aacagagttt ctagattgtc tcatttacgc caccactact caagaagtg    2160 gcacagattc aggtttaatc caaagtttta ttcatttctc tctgctcaag agccttccca    2220
caaaataggc actagcctgt cctcacttac tggaagtggg aagagaaata ggataagaag    2280
ttctctgcca tggaggcaaa atagttggaa agggtacagt gaaaacatga ggaagctcag    2340
aaagactcat gatattccat gcccagatct tccttggagc tataaaatag aataatttt    2400 cttcaagta ggttagctag ctctccccca ataaaaatac cactatcaga gtagaaacaa    2460
ggtagacatt tctaaaacat atgtgcttca ttatgaatcc atggatggct caattcttaa    2520
atgtaaatag atctctagga aactcaaagt acagtgtttt caatctaaaa agaagtattg    2580
gcagtttcac ttgcaaaatt acacagctgg tccctgtgat gtgtctcgac accaatacac    2640 aaccccctttc ccaccatcct tcatgtcact agatacacaa ccccccttccc accatccctt    2700 cagtcactag tggaagcttt caagttagtt atttcagtca ggatatacag tgttgaaatc    2760
tcaatgcagt tgaaatctgg tctgatgtgc ctaatttatc tgtggaaaat ttaatgctga    2820
attacatttg gttgggaaat gtccctcaaa atcctgggca ctatgaagga accccctgcc    2880
ccctcacctt tttgggtagg taaaagacta aaagccatat ggattttaac tgataacaat    2940
gaaagtggta aatcagtgta aagtgtcat attctcagac ttgtgaggcg gtttatagtc    3000
agaaagattt acggattttt ttcctgtaac ataaaagatt gtgaactttt tttaattaaa    3060
aaatatttcc tagggctgta gttatttggg agtttcataa cctgttatgg tgcttttggt    3120
ggaaattttt attatttagc attttaggag accgctgtca actggttta atctatgatg    3180 ctaatgtgtt ttccactgta ccctcatctc aggaataaaa ctgctttaac ggagatgatg    3240
tcaggtacaa atacactata gagtcaaaat accatttaca aagaaaatca aaagcatttc    3300
tatattttgt cttttttag ttcagacagc aaaggcatgt actactataa aatacaaagt    3360
```

```
gattttagag aatgaaaaat gctactttta tcttctctaa aattatttcc cccaaggtag    3420
tgaagtaatt ggaatgaagg aggctgaaag tattgtctaa agtgagccca gaggccactg    3480
agaatgcaga ttactgacag ccaggtctgt ttagttgtaa ttggaagaca catgagtgtc    3540
ctgcttacat gtagcttcag actgcagaga caggacgtgt gcttttcatt tcaatattta    3600
gttatatttg atattttgaa actgtctgct ttttgctatt tctgcagttt caagttagtt    3660
agaagcatgt tgtcaactaa agacaacaaa ctatcagatt cattcattca gtgaagcagc    3720
ctctgattct ctaagagtca cgaatgtctt agtgttaccc tcccctagtc aacagcagac    3780
cagcctggcc aatgcctatg ggtggcccct ctggagtgct cactaacaag ggtgagtgct    3840
ctcgctaaga agtgtccccc gcctaatcat gtgtttatag gatagtacac gttccccagg    3900
cccataacag aggactaaaa tctctgaatt ttaaagacac agatgactgg catattttgg    3960
ataccagtat agctatatca aatagacaaa aacagcttca ctttagcaat gatcagattg    4020
ttaatctaca gattttattt tttaaaattt ggatgtaagt agagactttc agtatttgtt    4080
ttctcttgat tttgaagtca tttcttcttc tcacgtctgt gacaaatggt tgaaaaggag    4140
tcaacatggc cccaactata gtgccggaac cttttcatca ttctgaggct ttgccccaca    4200
catggtcctc actcatatct gtcaccttct gaagcctaga tcttgttaac ccatcaggtg    4260
cagtgtcagt ttcaaatcaa attatctaag aaaacaagaa aacaaaggca gcagactatt    4320
ggtacacatt atagtccaaa gtgcttagcg aagtaaaaaa aaaagctttt taaaatttct    4380
attgttgtct attggtaatg ttttttgatca gaataaagag ggtaaaggga aaagttact    4440 acacatgcta ggctttctca gtggggaaaa aaatggctgg atagaactgg gacaaacaca    4500
gacccatctt taggggtctg gattttgtag gtccgactac acagcagtgt taactcattt    4560
ctcatgccat tagctctcta caaaataaag caaagtagtt ctagtgtggt cgttataaac    4620
caatattgtg aaaaatagca actattcatt tgttcacaac atgcgtattt atagagtagt    4680
taggtaccat ttgtaaggta aatcctttaa aattctataa tacatactaa aatagtggtt    4740
attggtctga tatatgctgc tcttggttct ataaactaga taaaagcagt gctttgtgaa    4800
atgcagtgtt ctctcttaac gccactggtg ataggaagta gttcccttca gttcaaatcc    4860
tgtgccctta tttgctgctt gctgacgtaa gcaataagta accctctaac taatggtatc    4920
tacatatttc tgtaacttgt atttaatgat ggtgtacctg gtgattgtaa aaatattaga    4980
cagatataaa agtatctata taatatctat aaactgttaa tgctgaggta tagtctgtga    5040
attatgtgtt ttgtattttt attcattgtg taatttagtg gtggtgaaag ttctacactc    5100
aatccttaaa gagtggcagt atccctttt caatttaaca tggtctgcat caatctgttt    5160
gcctgctaaa caagttagaa taggaaatag taaaataaat ccaaacaaga gtgtaatatt    5220
ggttagggaa acaaacttca ggtcaccaac tgaagtcatt acaaactcct tgtacattca    5280
ctgtgagttt caagggagt cagtccctaa tttacaggtt tcctttgttc actttctaga    5340
tgtgtacttt tgagggacat gaggttaggc aacattacag caacacacac tgggctatt    5400 aatcccattt aggtctgtac taagaggat gggtagaaac acatatgtat ataccttttc    5460
tttacctaga agtgccatcc attgtccttg aattattatg attaaagtta ctgttgcatt    5520
taggaggctc cttgaaagta acacctttc caaggacaat ggcaacaatg tcaatgtcaa    5580
cactgagtct aattttgacc acatttatag tggtatagtg tcaatactgc attttcatga    5640
caaccacact ccactgttga aacactgtgc cagtgagaag tgcaacatcc agtgggcaga    5700
tgaaaatgat gcatggccaa gttcagtgtt tacagataaa actgctgtgg ttcaagtgct    5760
```

| | |
|---|---|
| tccttcccca tcaaatcctt gataaggctt tgtgggaaaa tgatctaaat tattgtttta | 5820 |
| attttttaaac ctaatttatt cactcagtga acattcttac ctaagcaagg ctataaaagg | 5880 |
| gaatactaca gttttgtcca cactttaatt tgagaccatt tttctttgaa tcgtaagtta | 5940 |
| gcaaaagaaa ttttttttcac ctttgaaaat cacgtgatgt taaaggacaa atgcccactc | 6000 |
| ttctattctg atctgcaaat agcttaaatg tctcttgcaa aacaaagtaa gataccacca | 6060 |
| gtattacaac acaatgattt tccagacaaa tggtatggtg ttgaaaaata actgttactt | 6120 |
| cttaaagcag cattttatct tctatttttga agactattta ttgtaataat tagaaaacat | 6180 |
| gaaataggga actccagact gacacagcag ttgttttttga aaaggaaata aactttgatg | 6240 |
| aattagataa tccagataca tcattgtaaa ctcttactct aggtgctctt tggtgagaga | 6300 |
| caggctttgt tctcttgttc ataacatttc tctgcaaaga attctctatg gagtgaagcg | 6360 |
| aatgaagtga ataatttctt accaaataaa tttatcaatt tacaaatctg ctctacatct | 6420 |
| cacttttgag ttcagttgta gtcatgagtg atccttcata ttttattaaa agtgttcatt | 6480 |
| caggtaaggt gtatgttgaa attttgccaa ttatcttaat aaaacctggc aattt | 6535 |

<210> SEQ ID NO 4
<211> LENGTH: 2268
<212> TYPE: DNA
<213> ORGANISM: Homo sapiens

<400> SEQUENCE: 4

| | |
|---|---|
| atggccggct gcatccctga ggagaaaact taccggcgct tcctggagct attcctgggc | 60 |
| gagtttcgcg gaccgtgcgg cggcggcgag ccggagccgg aacccgaacc cgaacccgaa | 120 |
| cccgaacccg agtccgagcc cgagcccgaa cctgaactgg tagaagctga ggcggccgag | 180 |
| gcttcggtag aggaacccgg ggaggaggcg gccacggtag ccgcgacgga ggaggggac | 240 |
| caggagcaag acccggagcc cgaggaggag gcggcggttg agggtgagga ggaggaggag | 300 |
| ggcgcggcga cggcggcggc agccccgggg cactcggccg tgccgccgcc gccgcccag | 360 |
| ctgccgcctt tgcccccgct cccgcgaccg ctgtcagagc gcatcacccg cgaggaggtg | 420 |
| gagggcgaaa gcctggacct gtgcctgcag cagctctaca atataattg cccttccttt | 480 |
| ttggctgctg ctttagccag agccacatca gatgaagtcc ttcagagtga tctttctgca | 540 |
| cattatatcc caaaggaaac ggatggcaca gaagggactg tggagattga acagtgaaa | 600 |
| ttggcccgtt ctgtcttcag caaactacac gagatttgct gcagctgggt gaaagacttc | 660 |
| cccctccgca ggagacccca gctttattat gagacatcaa tccatgccat caaaaacatg | 720 |
| cgcaggaaaa tggaggacaa acatgtctgc attcctgact ttaatatgct cttcaaccta | 780 |
| gaggaccagg aagaacaagc ttactttgca gtgtttgatg gccatggggg agtagatgct | 840 |
| gctatttatg cctccattca cctccacgtt aacttagtcc gccaggagat gttcccccat | 900 |
| gatcctgctg aggccctgtg cagggccttc cgggtcactg atgagcggtt tgtgcagaaa | 960 |
| gcagccaggg agagcttaag atgtgggacc acaggagtgg tgactttcat cagaggcaac | 1020 |
| atgctacatg tggcctgggt gggtgattcc caggttatgc ttgtgagaaa gggccaagct | 1080 |
| gttgaactaa tgaagccaca caaaccagac agagaggatg aaaagcagag aattgaggcc | 1140 |
| cttggaggtt gcgtagtctg gtttggtgcc tgagggtga atggaagtct gtcggtttcc | 1200 |
| agagctattg gagatgctga acataagcca tatatctgtg gggatgcaga ttctgcctcc | 1260 |
| actgttctgg atgggaccga agactacctc attctggcct gtgatggctt ctatgacacc | 1320 |
| gtgaaccctg atgaggcagt gaaagttgtg tccgaccacc tgaaagagaa taatggagac | 1380 |

-continued

```
agcagcatgg ttgcccacaa attagtggca tcagctcgtg atgctgggtc aagtgataac    1440
atcacggtta ttgtggtatt cctgagggac atgaacaaag ctgtaaatgt tagtgaggaa    1500
tcagattgga cagagaactc ttttcaagga gggcaagaag atggtgggga tgataaggag    1560
aatcatggag agtgcaaacg cccttggcct cagcaccagt gctcagcacc agccgaccta    1620
ggctatgatg ggcgtgtgga ttcattcact gatagaacta gcctgagccc agggtcccaa    1680
atcaacgtgc tggaagaccc aggctaccta gatctcacac aaatagaagc aagcaaacct    1740
cacagtgccc agttttttgct accagttgag atgtttggtc ctggtgcacc aaagaaagca    1800
aatcttatta atgagttaat gatggagaaa aaatcagttc agtcatcatt gcctgaatgg    1860
agtggtgctg gagagtttcc cactgctttc aatttgggtt caacagggga gcagatatac    1920
agaatgcaga gcttgtctcc tgtctgttca gggttggaaa atgaacagtt caaatccccg    1980
ggaaacagag tttctagatt gtctcattta cgccaccact actcaaagaa gtggcacaga    2040
ttcaggttta atccaaagtt ttattcattt ctctctgctc aagagccttc ccacaaaata    2100
ggcactagcc tgtcctcact tactggaagt gggaagagaa ataggataag aagttctctg    2160
ccatggaggc aaaatagttg gaaagggtac agtgaaaaca tgaggaagct cagaaagact    2220
catgatattc catgcccaga tcttccttgg agctatataaaa tagaataa                2268
```

```
<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gttctggatg ggaccgaaga                                                   20

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
aaagttgtgt ccgaccacct g                                                 21

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
actgaagcac tacgggcctg                                                   20

<210> SEQ ID NO 8
<211> LENGTH: 19
<212> TYPE: DNA
<213> ORGANISM: Artificial
<220> FEATURE:
<223> OTHER INFORMATION: Primer

<400> SEQUENCE: 8
agccgttggt gtctttgcc                                                    19
```

PPM1E PROTEINS AND NUCLEIC ACIDS AS TARGETS FOR NEURODEGENERATIVE DISEASES

CROSS REFERENCE TO RELATED APPLICATIONS

This application is a U.S. national stage of Application No. PCT/EP08/064446, filed Oct. 24, 2008, which claims priority to U.S. Provisional Application No. 60/996,019, filed Oct. 25, 2007, and European Application No. 07119261.1, filed Oct. 25, 2007, all of which are herein incorporated by reference in their entirety.

BACKGROUND OF THE INVENTION

The present invention relates to assays and methods for identifying or for testing agents which are modulators of a serine-threonine phosphatase PPM1E and can be used for treating and/or preventing neurodegenerative disorders.

The present invention relates to methods of diagnosing, prognosticating and monitoring the progression of neurodegenerative diseases.

The present invention relates to the treatment and/or prevention of neurodegenerative disorders, more particularly to the treatment and/or prevention of Alzheimer's disease.

Neurodegenerative diseases, in particular Alzheimer's disease (AD), have a strongly debilitating impact on a patient's life. Furthermore, these diseases constitute an enormous health, social, and economic burden. AD is the most common neurodegenerative disease, accounting for about 70% of all dementia cases, and it is probably the most devastating age-related neurodegenerative condition affecting about 10% of the population over 65 years of age and up to 45% over age 85 (Wimo et al., *Alzheimer Dis. Assoc. Dis.* 2003, 17:63-67; Walsh and Selkoe, *Neuron* 2004, 44:181-193). Presently, this amounts to an estimated 12 million cases in the US, Europe, and Japan. This situation will inevitably worsen with the demographic increase in the number of old people in developed countries. The neuropathological hallmarks that occur in the brains of individuals with AD are senile plaques, composed of amyloid-β protein, and profound cytoskeletal changes coinciding with the appearance of abnormal filamentous structures and the formation of neurofibrillary tangles (Selkoe and Kopan, *Annu Rev Neurosci* 2003, 26:565-597; Saido and Iwata, *Neurosci. Res.* 2006, 54:235-253; Braak and Braak, *J Neural Transm* 1998, 53: 127-140; Schmitt et al., *Neurology* 2000, 55: 370-376).

Currently, there is no cure for AD, nor is there an effective treatment to halt the progression of AD or even to diagnose AD ante-mortem with high probability. Although there are rare examples of early-onset AD which have been attributed to genetic defects in the genes for amyloid precursor protein (APP) on chromosome 21, presenilin-1 on chromosome 14, and presenilin-2 on chromosome 1, the prevalent form of late-onset sporadic AD is of hitherto unknown etiologic origin. The late onset and complex pathogenesis of neurodegenerative disorders pose a formidable challenge to the development of therapeutic and diagnostic agents. It is crucial to expand the pool of drug targets and diagnostic markers.

It is therefore an object of the present invention to provide insight into the pathogenesis of neurodegenerative diseases and to provide methods, materials, agents and compositions which are suited inter alia for the diagnosis and the prevention and treatment of these diseases. This object has been solved by the features of the independent claims. The subclaims define preferred embodiments of the present invention.

The present invention discloses the use of a protein phosphatase 1 E (PPM1E) in methods for identifying or for testing agents for the treatment and/or prevention of neurodegenerative diseases and the use of PPM1E in diagnostic methods. A gene of the protein phosphatase 2C superfamily, coding for the protein phosphatase 1 E (PPM1E) and protein products thereof is dysregulated, is differentially expressed in human Alzheimer's disease brain samples. PPM1E has been formerly known as CaM kinase phophatase N (CaMKP-N) or as Partner of PIX 1 (POPX1); such formerly used gene symbols CaMKP-N or POPX1 have been exchanged to PPM1E in accordance with the HUGO (Human Genome Organisation) gene nomenclature.

Protein phosphatases are the counterparts of kinases in a variety of complex regulatory mechanisms of cellular functions like stress-activated signal transduction, mitogenic signal transduction, and cell cycle control. PPM1E is a serine-threonine phosphatase of 755 amino acids (84.0 kDa) that was identified as cDNA KIAA1072 in a project to accumulating basic information of unidentified human genes (Genbank accession number AB028995; REFSEQ accession number NM 014906; Kikuno et al., *DNA Res.* 1999, 6:197-205). The PPM1E gene is located on chromosome 17q22. PPM1E is also known as partner of PIX (POPX1) (Genbank accession number AF520614; Koh et al., *Current Biology* 2002, 12:317-321), as PP2CH (Genbank accession number AF260269; unpublished), and in the rat as nuclear calmodulin-dependent protein kinase phosphatase (CaMKP-N) (Genbank accession number AB081729; Takeuchi et al., *J. Biochem.* 2001, 130:833-840).

PPM1E was identified and characterized as substrate-specific phosphatase that dephosphorylates and concomitantly deactivates Ca2+/calmodulin-dependent protein kinases (CaMKs) such as CaMKI, CaMKII, and CaMKIV (Takeuchi et al., *J. Biochem.* 2001, 130:833-840). Enzymatic activity of PPM1E requires Mn2+ ions and is activated by polycations (Takeuchi et al., *J. Biochem.* 2001, 130:833-840; Ishida et al., *Arch. Biochem. Biophys.* 2002, 408:229-238). PPM1E was shown to be specifically expressed in brain (Takeuchi et al., *J. Biochem.* 2001, 130:833-840); in rat neurons PPM1E is present in the nucleus, in the cytoplasm and concentrated at synaptic sites (Kitani et al., *J. Neurochem.* 2006, 96:374-384). PPM1E exists in two forms, as full length protein carrying different nuclear localization signals at the C-terminus (Takeuchi et al., *J. Biochem.* 2004, 136:183-188), as well as a posttranslationally C-terminal truncated form of the full-length protein lacking amino acids 568-766 which include a nuclear localization signal (Kitani et al., *J. Neurochem.* 2006, 96:374-384). In addition to the CaMK-specific phosphatase activity it is reported that PPM1E forms a complex with Rho guanine nucleotide exchange factor 6 (ARHGEF6) and Serine/threonine-protein kinase PAK 1 (PAK1) and thereby antagonizes cdc42-mediated activation of PAK1 (Koh et al., *Current Biology* 2002, 12:317-321). A relation of PPM1E with neurodegenerative diseases, in particular with Alzheimer's disease, has not been disclosed so far.

BRIEF DESCRIPTION OF THE DRAWINGS

FIG. 1A lists the data for the identification of differences in the levels of PPM1E gene derived mRNA in human brain tissue samples from individuals corresponding to different Braak stages indicative for AD as measured by quantitative RT-PCR analysis.

FIG. 3A discloses SEQ ID NO: 1, the amino acid sequence of the human PPM1E full length protein.

FIG. 3B discloses SEQ ID NO: 2, the amino acid sequence of the human PPM1E posttranslationally truncated protein.

FIG. 4 shows SEQ ID NO: 3, the nucleotide sequence of the human PPM1E variant 1 cDNA.

FIG. 5 shows SEQ ID NO: 4, the coding sequence (cds) of the human PPM1E.

FIG. 13 schematically shows the separate evaluation of the pCaMKII alpha and pCaMKII beta bands of the western blots shown in FIG. 11.

SUMMARY OF THE INVENTION

Figure 1B:
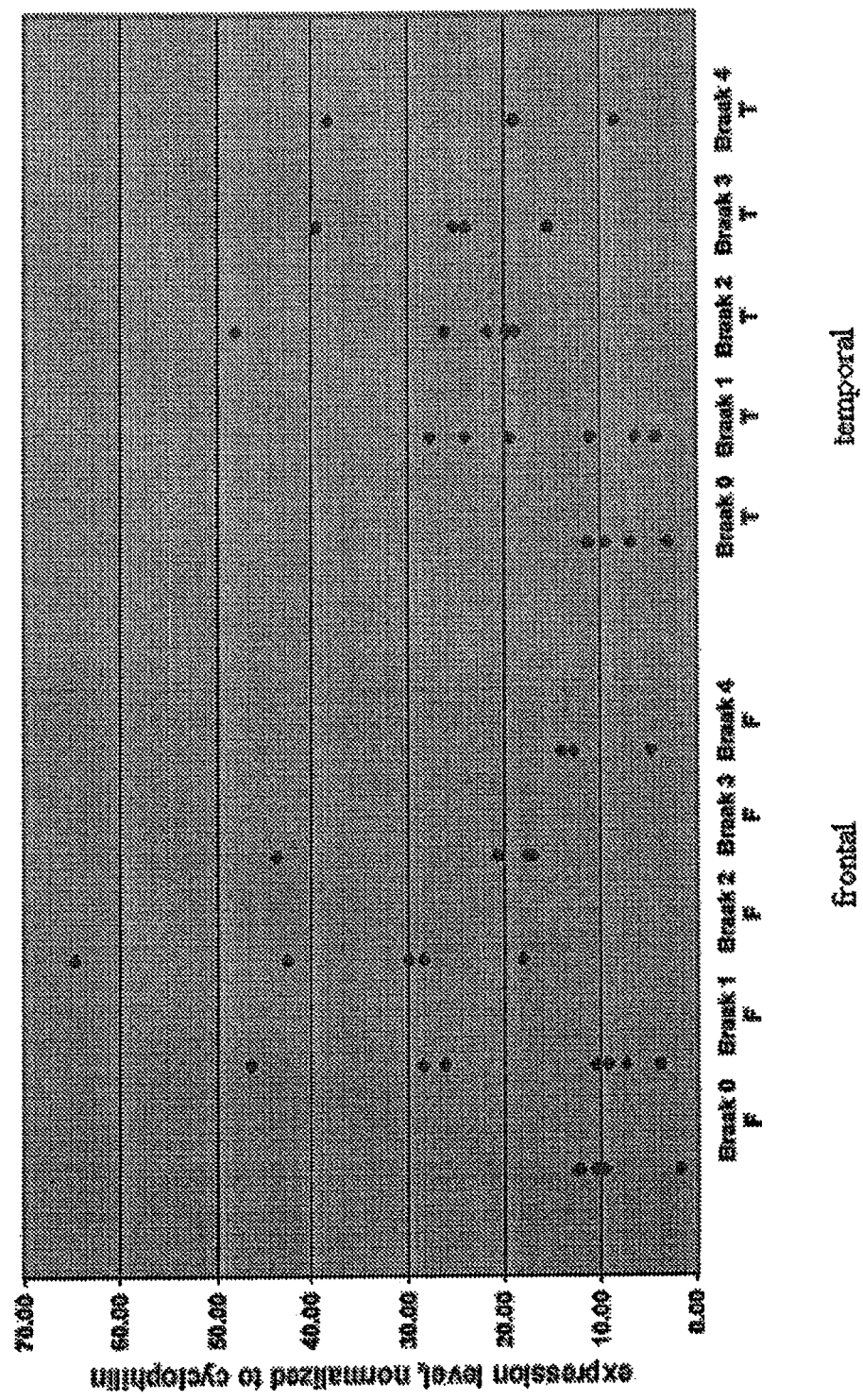
FIG. 1B demonstrates a substantial difference in gene expression level of PPM1E by comparison between samples representing different Braak stages.

The present invention provides methods for diagnosing, prognosticating and monitoring the progression of Alzheimer's disease, and for determining whether a subject is at increased risk of developing Alzheimer's disease. More particularly, the present invention provides assays and methods for the identification and for testing of agents binding, modulating a serine-threonine phosphatase PPM1E. Said agents are useful in the treatment and/or prevention of neurodegenerative disorders. The invention relates to the treatment and/or prevention of neurodegenerative disorders, particularly to the treatment of Alzheimer's disease using the PPM1E gene and/or its corresponding gene products and/or binding, modulating agents of the PPM1E gene and/or PPM1E gene products.

The singular forms "a", "an", and "the" as used herein and in the claims include plural reference unless the context dictates otherwise. For example, "a cell" means as well a plurality of cells, and so forth.

The term "and/or" as used in the present specification and in the claims implies that the phrases before and after this term are to be considered either as alternatives or in combination. For instance, the wording "determination of a level and/or an activity" means that either only a level, or only an activity, or both a level and an activity are determined.

The term "level" as used herein is meant to comprise a gage of, or a measure of the amount of, or a concentration of a substance such as a transcription product, for instance an mRNA, or a translation product, for instance a protein or polypeptide.

The term "activity" as used herein shall be understood as a measure for the ability of a substance, such as transcription product or a translation product to produce a biological effect or a measure for a level of biologically active molecules. The term "activity" also refers to biological activity and/or pharmacological activity which refer to binding, antagonization, repression, blocking, neutralization or sequestration of a transporter or transporter subunit and which refers to activation, agonization, and up-regulation of a transporter or transporter subunit. "Enzymatic" activity shall be the activity of an enzyme, as for example the activity of a phosphatase to dephosphorylate a phosphorylated substrate.

The terms "level" and/or "activity" as used herein further refer to gene expression levels or gene activity. Gene expression can be defined as the utilization of the information contained in a gene by transcription and translation leading to the production of a gene product. The measured "expression level" is an indicator for the amount of transcription or translation product produced.

"Dysregulation" shall mean an up-regulation, an increase, an elevation or a down-regulation, decrease, lowering of gene expression and/or an increase or decrease in the stability of the gene products. A "gene product" comprises either RNA or protein and is the result of expression of a gene. "Gene products" shall be any product, including full-length, fragments, derivatives, variants, posttranslationally truncated products, derived from the expression of a gene. The amount of a gene product can be used to measure how active a gene is and how stable its gene products are.

The term "gene" as used in the present specification and in the claims comprises both coding regions (exons) as well as non-coding regions (e.g. non-coding regulatory elements such as promoters or enhancers, introns, leader and trailer sequences).

The term "ORF" is an acronym for "open reading frame" and refers to a nucleic acid sequence that does not possess a stop codon in at least one reading frame and therefore can potentially be translated into a sequence of amino acids.

"Regulatory elements" shall comprise inducible and non-inducible promoters, enhancers, operators, and other elements that drive and regulate gene expression.

"Fragments" are understood to be any shorter or longer version of a gene, a gene product of the PPM1E gene, protein. The term "fragment" as used herein is meant to comprise e.g. an alternatively spliced, or truncated, or otherwise cleaved transcription product or translation product. For example, the proteins having SEQ ID NO: 1 and SEQ ID NO: 2 are translation products of the gene coding for PPM1E proteins and posttranslationally truncated products, fragments. The fragments on the nucleic acid level are coding for proteins which have still a comparable and significant functionality of the PPM1E proteins, the fragments on the protein level remain a comparable and significant functionality of the PPM1E proteins.

The term "derivative" as used herein refers to a mutant, or an RNA-edited, or a chemically modified, or otherwise altered transcription product, or to a mutant, or chemically modified, or otherwise altered translation product. For the purpose of clarity, a derivative transcript, for instance, refers to a transcript having alterations in the nucleic acid sequence such as single or multiple nucleotide deletions, insertions, or exchanges. A derivative translation product, for instance, may be generated by processes such as altered phosphorylation, or glycosylation, or acetylation, or lipidation, or by altered signal peptide cleavage or other types of maturation cleavage which may occur post-translationally. A posttranslationally truncated translation product is considered as a derivative of a translation product.

The term "modulator", "modulating agent", as used in the present invention and in the claims refers to a molecule, an agent capable of modulating, of regulating, of changing, altering the level and/or the activity of a gene, or a transcription product of a gene, or a translation product of a gene or any substrate of said gene product. A "modulator", "modulating agent" refers to a molecule which has the capacity to either increase, enhance or decrease, inhibit, thus to "modulate" a functional property of a protein, to "modulate" binding, antagonization, repression, blocking, neutralization or sequestration, activation, agonization and regulation. "Modulation" will be also used to refer to the capacity to affect the biological activity of a cell. Preferably, a "modulator" is capable of changing or altering the biological activity of a transcription product or a translation product of a gene. Said modulation, for instance, may be an increase or a decrease in the biological activity and/or pharmacological activity, a change in binding characteristics, or any other change or alteration in the biological, functional, or immunological properties of said translation product of a gene.

The terms "agent", "reagent", or "compound" refer to any substance, chemical, composition, or extract that have a positive or negative biological effect on a cell, tissue, body fluid, a substrate, another molecule, or within the context of any biological system, or any assay system examined. They can be agonists, antagonists, partial agonists or inverse agonists of a target. Such agents, reagents, or compounds may be nucleic acids, natural or synthetic peptides or protein complexes, or fusion proteins. They may also be antibodies, organic or anorganic molecules or compositions, small molecules, drugs and any combinations of any of said agents above. They may be used for testing, for diagnostic or for therapeutic purposes and for screening methods.

The terms "oligonucleotide primer" or "primer" refer to short nucleic acid sequences which can anneal to a given target polynucleotide by hybridization of the complementary base pairs and can be extended by a polymerase. They may be chosen to be specific to a particular sequence or they may be randomly selected, e.g. they will prime all possible sequences in a mix. The length of primers used herein may vary from 10 nucleotides to 80 nucleotides. "Probes" are short nucleic acid sequences of the nucleic acid sequences described and disclosed herein or sequences complementary therewith. They may comprise full length sequences, or fragments, derivatives, isoforms, or variants of a given sequence. The identification of hybridization complexes between a "probe" and an assayed sample allows the detection of the presence of other similar sequences within that sample.

As used herein, "homolog or homology" is a term used in the art to describe the relatedness of a nucleotide or peptide sequence to another nucleotide or peptide sequence, which is determined by the degree of identity and/or similarity between said sequences compared.

In the art, the terms "identity" and "similarity" mean the degree of polypeptide or polynucleotide sequence relatedness which are determined by matching a query sequence and other sequences of preferably the same type (nucleic acid or protein sequence) with each other. Preferred computer program methods to calculate and determine "identity" and "similarity" include, but are not limited to GCG BLAST (Basic Local Alignment Search Tool) (Altschul et al., *J. Mol. Biol.* 1990, 215: 403-410; Altschul et al., *Nucleic Acids Res.* 1997, 25: 3389-3402; Devereux et al., *Nucleic Acids Res.* 1984, 12: 387), BLASTN 2.0 (Gish W., 1996-2002), FASTA (Pearson and Lipman, *Proc. Natl. Acad. Sci. USA* 1988, 85: 2444-2448), and GCG GelMerge which determines and aligns a pair of contigs with the longest overlap (Wilbur and Lipman, *SIAM J. Appl. Math.* 1984, 44: 557-567; Needleman and Wunsch, *J. Mol. Biol.* 1970, 48: 443-453).

The term "variant" as used herein refers to any polypeptide or protein, in reference to polypeptides and proteins disclosed in the present invention, in which one or more amino acids are added and/or substituted and/or deleted and/or inserted at the N-terminus, and/or the C-terminus, and/or within the native amino acid sequences of the native polypeptides or proteins of the present invention, but retains its essential properties. Furthermore the term "variant" as used herein refers to any mRNA, in reference to gene transcripts disclosed in the present invention, in which one or more nucleotides are added and/or substituted and/or deleted.

Furthermore, the term "variant" shall include any shorter or longer version of a polypeptide or protein. "Variants" shall also comprise a sequence that has at least about 80% sequence identity, more preferably at least about 85% sequence identity, and most preferably at least about 90% sequence identity over a length of at least 200 amino acids of PPM1E proteins having SEQ ID NO: 1, or SEQ ID NO: 2: or of fragments of said PPM1E proteins. "Variants" also include, for example, proteins with conservative amino acid substitutions in highly conservative regions.

Furthermore, the term "variant" shall include any shorter or longer version of a gene transcript, of a translation product. "Variants" shall also comprise a sequence that has at least about 80% sequence identity, more preferably at least about 85% sequence identity, and most preferably at least about 90% sequence identity over a length of at least 600 nucleotides of PPM1E gene transcripts having SEQ ID NO: 3, or SEQ ID NO: 4 or of fragments of said PPM1E gene transcripts. Sequence variations shall be included wherein a codon is replaced with another codon due to alternative base sequences, but the amino acid sequence translated by the DNA sequence remains unchanged. This known in the art phenomenon is called redundancy of the set of codons which translate specific amino acids.

"Proteins and polypeptides" of the present invention include variants, fragments and chemical derivatives of the proteins comprising the amino acid sequences of PPM1E proteins having SEQ ID NO: 1, or SEQ ID NO: 2. Included shall be such exchange of amino acids which would have no effect on functionality, such as arginine for lysine, valine for leucine, asparagine for glutamine. Proteins and polypeptides can be included which can be isolated from nature or be produced by recombinant and/or synthetic means. Native proteins or polypeptides refer to naturally-occurring truncated or secreted forms, naturally occurring variant forms (e.g. splice-variants) and naturally occurring allelic variants.

The term "isolated" as used herein is considered to refer to molecules or substances which have been changed and/or that are removed from their natural environment, i.e. isolated from a cell or from a living organism in which they normally occur, and that are separated or essentially purified from the coexisting components with which they are found to be associated in nature. This notion further means that the sequences encoding such molecules can be linked by the hand of man to polynucleotides, to which they are not linked in their natural state and such molecules can be produced by recombinant and/or synthetic means, it is also said that they are "non-native". Even if for said purposes those sequences may be introduced into living or non-living organisms by methods known to those skilled in the art, and even if those sequences are still present in said organisms, they are still considered to be isolated. In the present invention, the terms "risk", "susceptibility", and "predisposition" are tantamount and are used with respect to the probability of developing a neurodegenerative disease, preferably Alzheimer's disease.

"Neurodegenerative diseases or disorders" according to the present invention comprise Alzheimer's disease, Parkinson's disease, Huntington's disease, amyotrophic lateral sclerosis, Pick's disease, fronto-temporal dementia, progressive nuclear palsy, corticobasal degeneration, cerebro-vascular dementia, multiple system atrophy, argyrophilic grain dementia and other tauopathies, and mild-cognitive impairment. Further conditions involving neurodegenerative processes are, for instance, ischemic stroke, age-related macular degeneration, narcolepsy, motor neuron diseases, prion diseases, traumatic nerve injury and repair, and multiple sclerosis.

The term "AD" shall mean Alzheimer's disease. "AD-type neuropathology", "AD pathology" as used herein refers to neuropathological, neurophysiological, histopathological and clinical hallmarks, signs and symptoms as described in the instant invention and as commonly known from state-of-the-art literature (see: Iqbal, Swaab, Winblad and Wisniewski, *Alzheimer's Disease and Related Disorders (Etiology, Pathogenesis and Therapeutics)*, Wiley & Sons, New York, Weinheim, Toronto, 1999; Scinto and Daffner, *Early Diagnosis of Alzheimer's Disease*, Humana Press, Totowa, N.J., 2000; Mayeux and Christen, *Epidemiology of Alzheimer's Disease: From Gene to Prevention*, Springer Press, Berlin, Heidelberg, New York, 1999; Younkin, Tanzi and Christen, *Presenilins and Alzheimer's Disease*, Springer Press, Berlin, Heidelberg, New York, 1998).

The term "Braak stage" or "Braak staging" refers to the classification of brains according to the criteria proposed by Braak and Braak (Braak and Braak, *Acta Neuropathology* 1991, 82: 239-259). Braak staging of AD rates the extent and distribution of neurofibrillary pathology in determined regions of the forebrain and divides the neuropathologic progression of AD into six stages (stage 0 to 6). It is a well established and universally accepted procedure in post-mortem neuropathological staging of AD. It has convincingly been shown that there is a significant correlation between an AD patient's clinical condition with respect to mental status and cognitive function/impairment and the corresponding Braak stage obtained after autopsy (Bancher et al., *Neuroscience Letters* 1993, 162:179-182; Gold et al., *Acta Neuropathol.* 2000, 99: 579-582). Likewise, a correlation between neurofibrillary changes and neuronal cellular pathology has been found (Rössler et al., *Acta Neuropathol.* 2002, 103:363-369), and both have been reported to predict cognitive function (Giannakopoulos et al., Neurology 2003, 60:1495-1500; Bennett et al., *Arch. Neurol.* 2004, 61:378-384). Moreover, a pathogenic cascade has been proposed that involves the deposition of beta-amyloid peptide and finally cumulates in the formation of neurofibrillary tangles, the latter thus witnessing the precedence of earlier AD-specific events at the molecular/cellular level (Metsaars et al., *Neurobiol. Aging* 2003, 24:563-572).

In the instant invention, Braak stages are therefore used as a surrogate marker of disease progression independent of the clinical presentation/condition of the individual donor, i.e. independent of the presence or absence of reported mental illness, cognitive deficits, decline in other neuropsychiatric parameters, or the overt clinical diagnosis of AD. I.e. it is presumed that the neurofibrillary changes on which the Braak staging reflect the underlying molecular and cellular pathomechanisms in general and hence define a (pre-)morbid condition of the brain, meaning that e.g. a donor staged Braak 1 represents by definition an earlier stage of molecular/cellular pathogenesis than a donor staged 2 (or higher), and that therefore a donor of Braak stage 1 can e.g. be regarded as a control individual when compared to donors of any higher Braak stage. In this regard, the differentiation between control individual and affected individual may not necessarily be the same as the clinical diagnosis based differentiation between healthy control donor and AD patient, but it rather refers to a presumed difference in the (pre-) morbid status as deduced from and mirrored by a surrogate marker, the Braak stage.

In the instant invention Braak stage 0 may represent persons which are not considered to suffer from Alzheimer's disease signs and symptoms, and Braak stages 1 to 4 may represent either healthy control individuals or AD patients depending on whether said individuals were suffering already from clinical signs and symptoms of AD. The higher the Braak stage the more likely is the possibility to display signs and symptoms of AD or the risk to develop signs and symptoms of AD. For a neuropathological assessment, i.e. an estimation of the probability that pathological changes of AD are the underlying cause of dementia, a recommendation is given by Braak H (Braak and Braak, *Acta Neuropathology* 1991, 82: 239-259).

The values obtained from controls are the reference values representing a known health status and the values obtained from patients are the reference values representing a known disease status.

DETAILED DESCRIPTION OF THE INVENTION

The gene of the protein phosphatase 1E, also named PPM1E, and the gene products of said gene PPM1E, are differentially expressed, differentially regulated, dysregulated in specific samples, in specific brain regions of AD patients, in specific brain regions of individuals grouped into different Braak stages, in comparison with each other and/or in comparison to age-matched control individuals. The gene expression for PPM1E is varied, is dysregulated in brains of AD patients as compared to the respective brain regions of control individuals, in that PPM1E mRNA levels are increased, are up-regulated in the inferior temporal cortex and in the frontal cortex of AD patients compared to controls. Further, PPM1E expression differs in specific brain regions of individuals grouped into different Braak stages with an increase in expression level starting already at early Braak stages and with a progressive increase with the course of Braak stages (Braak 1-3).

Linking the PPM1E gene to diseases as for example Alzheimer's disease offers new ways, inter alia, for the diagnosis and prevention and treatment of said diseases. Linking PPM1E to pathological events occurring already early in the course of AD provides the possibility of a treatment which will prevent the initiation of AD pathology, a treatment which will be applied before non-repairable damages of the brain occur. Consequently, the present invention has utility for diagnostic evaluation, for diagnostic monitoring of persons undergoing a treatment, for prognosis as well as for the identification of a predisposition to a neurodegenerative disease, in particular AD. Furthermore, the present invention has utility for using PPM1E in assays and in methods for identifying and for testing agents, modulators, which are useful in the treatment and prevention of neurodegenerative disorders.

Neurons within the inferior temporal lobe, the entorhinal cortex, the hippocampus, and the amygdala, thus, neurons within specific brain regions are subject to degenerative processes in AD (Terry et al., *Annals of Neurology* 1981, 10:184-192). These brain regions are mostly involved in the processing of learning and memory functions and display a selective vulnerability to neuronal loss and degeneration in AD. Brain tissues from the frontal cortex (F) and the inferior temporal cortex (T) of AD patients and of age-matched controls were used for herein described examples. Consequently, the PPM1E gene and its corresponding transcription and/or translation products play a causative role, and/or have an influence on the selective neuronal degeneration.

In one aspect, the invention features a method of diagnosing or prognosticating a neurodegenerative disease in a subject, or of determining whether a subject has a predisposition of developing said disease, is at increased risk of developing said disease, or of monitoring the effect of a treatment administered to a subject having a neurodegenerative disease. The method comprises: determining a level, an expression or an activity, or both said level, expression and said activity of (i) a transcription product of a gene coding for PPM1E proteins, and/or of (ii) a translation product of a gene coding for PPM1E proteins, and/or of (iii) a fragment, or derivative, or variant of said transcription or translation product in a sample obtained from said subject and comparing said level, expression and/or said activity of said transcription product and/or said translation product and/or said fragment, derivative or variant thereof to a reference value representing a known disease status (patient) and/or to a reference value representing a known health status (control), and/or to a reference value representing a known Braak stage and analysing whether said level and/or said activity is varied, is altered compared to a reference value representing a known health status, and/or is similar or equal to a reference value representing a known disease status and/or is similar compared to a reference value representing a known Braak stage which is an indication that said subject has a neurodegenerative disease, or that said subject is at increased risk of developing signs and symptoms of said disease, thereby diagnosing or prognosticating said neurodegenerative disease in said subject, or determining whether said subject is at increased risk of developing said neurodegenerative disease.

The wording "in a subject" refers to results of the methods disclosed as far as they relate to a disease afflicting a subject, that is to say, said disease being "in" a subject.

In a further aspect, the invention features a method of monitoring the progression of a neurodegenerative disease in a subject. A level, expression or an activity, or both said level, expression and said activity, of (i) a transcription product of a gene coding for PPM1E proteins, and/or of (ii) a translation product of a gene coding for PPM1E proteins, and/or of (iii) a fragment, or derivative, or variant of said transcription or translation product in a sample obtained from said subject is determined. Said level, expression and/or said activity are compared to a reference value representing a known disease or health status or a known Braak stage. Thereby, the progression of said neurodegenerative disease over a period of time in said subject is monitored.

In still a further aspect, the invention features a method of evaluating a treatment or monitoring the effect of a treatment for a neurodegenerative disease, comprising determining a level, expression or an activity, or both said level, expression and said activity of (i) a transcription product of a gene coding for PPM1E proteins, and/or of (ii) a translation product of a gene coding for PPM1E proteins, and/or of (iii) a fragment, or derivative, or variant of said transcription or translation product in a sample obtained from a subject being treated for said disease. Said level, expression or said activity, or both said level, expression and said activity are compared to a reference value representing a known disease or health status or a known Braak stage which was not subject of a treatment, thereby evaluating the treatment for said neurodegenerative disease.

In a preferred embodiment of said method of monitoring, method of evaluating, of monitoring the effect of a treatment, the level, expression or the activity, or both said level and said activity of (i) a transcription product of a gene coding for PPM1E proteins, and/or of (ii) a translation product of a gene coding for PPM1E proteins, and/or of (iii) a fragment, or derivative, or variant of said transcription or translation product in a series of samples taken from said subject over a period of time is compared, in order to monitor the progression of said disease. In further preferred embodiments, said subject receives a treatment prior to one or more of said sample gatherings. In yet another preferred embodiment, said level and/or activity is determined before and after said treatment of said subject.

It is preferred that said level, the expression and/or said activity of said transcription product and/or said translation product of PPM1E and of its fragments, derivatives, or variants, is increased, is up-regulated in samples obtained from AD patients as compared to samples obtained from persons not suffering from AD, control persons. For example, the expression and/or activity of the transcription product and/or the translation product of PPM1E and of its fragments, derivatives, or variants is measured from samples of patients and compared with the expression and/or activity of the transcription product and/or the translation product of PPM1E and of its fragments, derivatives, or variants in a sample of a healthy control subject (reference sample).

In a preferred embodiment of the herein claimed uses, assays, methods, methods of diagnosing, methods of identifying, methods of testing, methods of screening, herein claimed kits, agents and materials of the instant invention, said PPM1E gene codes for proteins having SEQ ID NO: 1, variant or derivative or fragment no. 1 (full length protein of PPM1E, RefSeq primary accession number NP_055721, Ensembl primary accession number ENSP00000312411), or SEQ ID NO: 2, variant or derivative or fragment no. 2 (post-translationally truncated protein of PPM1E NP_055721). The amino acid sequences of said variants are deduced from the mRNA sequences of SEQ ID NO: 3 which correspond to the cDNA sequence of Ensembl transcript ID number ENST00000308249. In the instant invention PPM1E also refers to the nucleic acid sequences SEQ ID NO: 4 representing the coding sequences (cds) of human PPM1E. In the instant invention said sequences are "isolated" as the term is employed herein. Further, in the instant invention, the gene coding for said PPM1E proteins (full length form and post-translationally truncated form) is also generally referred to as the PPM1E gene or simply PPM1E.

In a further preferred embodiment of the herein claimed methods, assays, kits, agents, materials and uses of the instant invention, PPM1E variants, fragments, derivatives comprising a sequence having at least about 80% sequence identity, more preferably at least about 85% sequence identity, and most preferably at least about 90% sequence identity of PPM1E proteins having SEQ ID NO: 1 or SEQ ID NO: 2 and having phosphatase activity are disclosed and in a particular embodiment, PPM1E variants deposited as accession numbers AF520614, AB028995, AF260269, and CR749253, that are cross-referenced to the UniProt primary accession number Q8WY54-2 and having phosphatase activity are disclosed.

In a further preferred embodiment of the herein claimed methods, assays, kits, agents, materials and uses of the instant invention, said neurodegenerative disease or disorder is Alzheimer's disease, and said subjects may suffer from signs and symptoms of Alzheimer's disease.

It is preferred that the sample to be analyzed and determined is selected from the group comprising brain tissue or other tissues, or body cells. The sample can also comprise cerebrospinal fluid or other body fluids including saliva, urine, stool, blood, serum plasma, or mucus. Preferably, the methods of diagnosis, prognosis, monitoring the progression or evaluating a treatment for a neurodegenerative disease, according to the instant invention, can be practiced ex corpore, and such methods preferably relate to samples, for instance, body fluids or cells, removed, collected, or isolated from a subject or patient or a control person.

In further preferred embodiments, said reference value is that of a level, of expression, or of an activity, or both of said level and said activity of (i) a transcription product of the gene coding for PPM1E proteins, and/or of (ii) a translation product of the gene coding for PPM1E proteins, and/or of (iii) a fragment, or derivative, or variant of said transcription or translation product in a sample obtained from a subject not suffering from said neurodegenerative disease (control sample, control, healthy control person) or in a sample obtained from a subject suffering from a neurodegenerative disease, in particular Alzheimer's disease (patient sample, patient, AD sample) or from a person with a defined Braak stage which may suffer or may not suffer from signs and symptoms of AD.

In preferred embodiments, an alteration in the level and/or activity and/or expression of a transcription product of the gene coding for PPM1E proteins and/or of a translation product of the gene coding for PPM1E proteins and/or of a fragment, or derivative, or variant thereof in a sample cell, or tissue, or body fluid taken from said subject relative to a reference value representing a known health status (control sample) indicates a diagnosis, or prognosis, or increased risk of becoming diseased with a neurodegenerative disease, particularly AD.

In a further preferred embodiment, an equal or similar level and/or activity and/or expression of a transcription product of the gene coding for PPM1E proteins and/or of a translation product of the gene coding for PPM1E proteins and/or of a fragment, or derivative, or variant thereof in a sample cell, or tissue, or body fluid obtained from a subject relative to a reference value representing a known disease status of a neurodegenerative disease, in particular Alzheimer's disease (AD patient sample), indicates a diagnosis, or prognosis, or increased risk of becoming diseased with said neurodegenerative disease.

In another further preferred embodiment, an equal or similar level, expression and/or activity of a transcription product of the gene coding for PPM1E proteins and/or of a translation product of the gene coding for PPM1E proteins and/or of a fragment, or derivative, or variant thereof in a sample cell, or tissue, or body fluid obtained from a subject relative to a reference value representing a known Braak stage which Braak stage reflects a high risk of developing signs and symptoms of AD, indicates a diagnosis, or prognosis, or an increased risk of becoming diseased with AD.

It is preferred however that said varied, altered level, altered expression and/or said altered activity of said transcription product and/or said translation product of PPM1E and of its fragments, derivatives, or variants, is an increase, an up-regulation.

In preferred embodiments, measurement of the level of transcription products and/or of expression of the gene coding for PPM1E proteins is performed in a sample obtained from a subject using a quantitative PCR-analysis with primer combinations to amplify said gene specific sequences from cDNA obtained by reverse transcription of RNA extracted from a sample of a subject. Primer combinations (SEQ ID NO: 5, SEQ ID NO: 6) are given in Example 1 (iii) of the instant invention, but also other primers generated from the sequences as disclosed in the instant invention can be used. A Northern blot or a ribonuclease protection assay (RPA) with probes specific for said gene can also be applied. These techniques are known to those of ordinary skill in the art (see Sambrook and Russell, *Molecular Cloning: A Laboratory Manual*, Cold Spring Harbor Laboratory Press, Cold Spring Harbor, N.Y., 2001). An example of an immunoassay is the detection and measurement of enzyme activity as disclosed and described in the patent application WO02/14543.

The invention also relates to the construction and the use of primers and probes which are unique to the nucleic acid sequences, or fragments, or variants thereof, as disclosed in the present invention. The oligonucleotide primers and/or probes can be labeled specifically with fluorescent, bioluminescent, magnetic, or radioactive substances. The invention further relates to the detection and the production of said nucleic acid sequences, or fragments and variants thereof, using said specific oligonucleotide primers in appropriate combinations. PCR-analysis, a method well known to those skilled in the art, can be performed with said primer combinations to amplify said gene specific nucleic acid sequences from a sample containing nucleic acids. Such sample may be derived either from healthy or diseased subjects or subjects with defined Braak stages. Whether an amplification results in a specific nucleic acid product or not, and whether a fragment of different length can be obtained or not, may be indicative for a neurodegenerative disease, in particular Alzheimer's disease. Thus, the invention provides nucleic acid sequences, oligonucleotide primers, and probes of at least 10 bases in length up to the entire coding and gene sequences, useful for the detection of gene mutations and single nucleotide polymorphisms in a given sample comprising nucleic acid sequences to be examined, which may be associated with neurodegenerative diseases, in particular Alzheimer's disease. This feature has utility for developing rapid DNA-based diagnostic tests, preferably also in the format of a kit. Primers for PPM1E are exemplarily described in Example 1 (iii).

In another aspect, the invention features a kit for the methods of diagnosing, of prognosticating neurodegenerative diseases in a subject, or determining the propensity or predisposition of a subject to develop a neurodegenerative disease, or of monitoring the effect of a treatment administered to a subject having a neurodegenerative disease, said kit comprising:
(a) at least one reagent which is selected from the group consisting of (i) reagents that selectively detect a transcription product of the gene coding for PPM1E proteins (ii) reagents that selectively detect a translation product of the gene coding for PPM1E proteins; and/or (iii) reagents that detect a fragment or derivative or variant of said transcription or translation product;

(b) an instruction describing a method for diagnosing, or prognosticating a neurodegenerative disease, or determining the propensity or predisposition of a subject to develop such a disease or of monitoring the effect of a treatment as disclosed in the instant invention.

The kit, according to the present invention, may be particularly useful for the identification of individuals that are at risk of developing a neurodegenerative disease, which neurodegenerative disease is in particular AD.

Reagents that selectively detect a transcription product and/or a translation product of the gene coding for PPM1E proteins, preferably coding for the variants having SEQ ID NO: 1, or having SEQ ID NO: 2, can be sequences of various length, fragments of sequences, antibodies, aptamers, siRNA, microRNA, and ribozymes. Such reagents may be used also to detect fragments, derivatives or variants thereof.

In a further aspect the invention features the use of a kit in a method of diagnosing or prognosticating a neurodegenerative disease, in particular Alzheimer's disease, in a subject, and in a method of determining the propensity or predisposition of a subject to develop such a disease, and in a method of monitoring the effect of a treatment administered to a subject having a neurodegenerative disease, particularly AD.

Consequently, the kit, according to the present invention, may serve as a means for targeting identified individuals for early preventive measures or therapeutic intervention prior to disease onset, before irreversible damage in the course of the disease has been inflicted. Furthermore, in preferred embodiments, the kit featured in the invention is useful for monitoring a progression of a neurodegenerative disease, in particular AD in a subject, as well as monitoring success or failure of therapeutic treatment for such a disease of said subject.

Furthermore, a level and/or an activity and/or expression of a translation product of the gene coding for PPM1E proteins and/or of a fragment, or derivative, or variant of said translation product, and/or the level or activity of said translation product, and/or of a fragment, or derivative, or variant thereof, can be detected and determined using a binding assay, an immunoassay, an activity assay, a cellular assay. Activity assays can measure the enzymatic activity of a protein, for example the phosphatase activity in an appropriate phosphatase assay measuring the dephosphorylation of a phosphorylated substrate (EP01199370). Examples of such activity assays, cellular assay are given in the instant invention (example 2 and example 3). Binding assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, *Antibodies: A Laboratory Manual*, Cold Spring Harbor Laboratory Press, Cold Spring Harbor, N.Y., 1999 and Edwards R, *Immunodiagnostics: A Practical Approach*, Oxford University Press, Oxford; England, 1999). All these detection techniques may also be employed in the format of microarrays, protein-arrays, antibody microarrays, tissue microarrays, electronic biochip or protein-chip based technologies (see Schena M., *Microarray Biochip Technology*, Eaton Publishing, Natick, Mass., 2000).

In one aspect, the invention features the use of (i) a gene coding for a protein phosphatase 1 E, and/or of (ii) a transcription product of the gene coding for a protein phosphatase 1 E, and/or of (iii) a translation product of the gene coding for a protein phosphatase 1 E, and/or of (iv) a fragment, or derivative, or variant of (i) to (iii) for identifying agents or for testing agents for the treatment and/or prevention of neurodegenerative diseases. Said agents identified and/or tested are modulators of (i) to (iv). It is preferred that said gene coding for a protein phosphatase 1 E is the gene coding for a protein phosphatase 1 E protein having SEQ ID NO:1 or SEQ ID NO: 2 and/or wherein said translation product of the gene coding for a protein phosphatase 1 E proteins is the protein phosphatase 1 E protein having SEQ ID NO: 1 or SEQ ID NO: 2. It is further preferred that said neurodegenerative disease is Alzheimer's disease.

In preferred embodiment the use of (i) a gene coding for a protein phosphatase 1 E, and/or of (ii) a transcription product of the gene coding for a protein phosphatase 1 E, and/or of (iii) a translation product of the gene coding for a protein phosphatase 1 E, and/or of (iv) a fragment, or derivative, or variant of (i) to (iii) is in a method of a binding assay, an immunoassay, an activity assay or a cellular assay. Examples of said methods are disclosed in Example 2 and Example 3.

In another aspect, the invention features a method for identifying agents for the treatment and/or prevention of neurodegenerative diseases, in particular AD, or related diseases and disorders. Said method comprises (a) contacting an agent with a phosphorylated substrate and with a protein phosphatase 1 E and/or a fragment, or derivative, or variant thereof, (b) measuring the enzymatic activity of a protein phosphatase 1 E, and/or a fragment, or derivative, or variant thereof, (c) comparing the enzymatic activity measured in step (b) with the enzymatic activity of a protein phosphatase 1 E, and/or a fragment, or derivative, or variant thereof not contacted with said agent, (d) identifying agents modulating the enzymatic activity of a protein phosphatase 1 E and/or a fragment, or derivative, or variant thereof as agents for the treatment and/or prevention of neurodegenerative disorders.

In a further aspect of the method for identifying agents for the treatment and/or prevention of neurodegenerative diseases said (a) contacting of an agent with a phosphorylated substrate and with a protein phosphatase 1 E and/or a fragment, or derivative, or variant thereof is in a sample wherein the sample is an in vitro sample comprising an expression system for expression of PPM1E or is a cell, a tissue, or a non-human animal comprising an expression system for expression of PPM1E or is a cell, a tissue, or a non-human animal expressing PPM1E. Cells expressing or overexpressing a protein PPM1E and the use thereof are disclosed in Example 2 and 3.

In a further aspect, said method of identifying agents for the treatment and/or prevention of neurodegenerative diseases by measuring the enzymatic activity of a protein phosphatase 1 E is as well suitable for testing agents, said testing may be a conformation testing of agents unknown or of agents already known in the context of neurodegenerative disorders.

In a preferred embodiment said agents identified are modulators having the ability to modulate, to alter the binding capacity, the expression, the functionality and/or to alter the enzymatic activity of a PPM1E protein (preferably having SEQ ID NO: 1 or SEQ ID NO: 2), and/or a fragment, or derivative, or variant thereof.

In a further preferred embodiment said enzymatic activity measured is a phosphatase activity. Said phosphatase activity is measured by determination of the dephosphorylation of a phosphorylated substrate, preferably a substrate peptide. Said substrate can be a fluorescently labelled or non-labelled substrate. The determination of the phosphorylation status of the phosphorylated substrate can be by measuring the binding of a sustrate specific antibody, by measuring the fluorescence.

In a preferred embodiment of said methods of identifying or of testing agents for the treatment and/or prevention of neurodegenerative diseases said agents are identified or tested which decrease the enzymatic activity of a protein phosphatase 1 E.

In a further preferred embodiment of said methods of identifying or of testing agents for the treatment and/or prevention of neurodegenerative diseases said agents are identified or tested which inhibit the enzymatic activity of a protein phosphatase 1 E.

In another aspect, the invention features a method for identifying agents for the treatment and/or prevention of neurodegenerative diseases, in particular AD, or related diseases and disorders. Said method comprises (a) contacting a sample comprising an expression system for expression of a protein phosphatase 1E with an agent, (b) measuring an expression level of a gene coding for a PPM1E protein, and/or a transcription product of the gene coding for a PPM1E protein and/or a fragment, or derivative, or variant thereof, in said sample, (c) comparing the expression level measured in step (b) with an expression level of gene coding for a PPM1E protein, and/or a transcription product of the gene coding for PPM1E protein and/or a fragment, or derivative, or variant thereof measured in a sample comprising an expression system for expression of a protein phosphatase 1E not contacted with said agent, (d) identifying agents modulating the expression level of a gene coding for a PPM1E protein, and/or a transcription product of the gene coding for a PPM1E protein and/or a fragment, or derivative, or variant thereof as agents for the treatment and/or prevention of neurodegenerative disorders.

In a further aspect of the method for identifying agents for the treatment and/or prevention of neurodegenerative diseases said sample comprising an expression system for expression of a protein phosphatase 1E is an in vitro sample or is a cell, a tissue, or a non-human animal comprising an expression system for expression of PPM1E.

In a further aspect, said method of identifying agents for the treatment and/or prevention of neurodegenerative diseases by measuring an expression level of a gene coding for a PPM1E protein, and/or a transcription product of the gene coding for PPM1E protein and/or a fragment, or derivative, or variant thereof is as well suitable for testing agents, said testing may be a conformation testing of agents unknown or of agents already known in the context of neurodegenerative disorders.

In a preferred embodiment of said method of identifying or of testing agents for the treatment and/or prevention of neurodegenerative diseases said agents are identified or tested which decrease an expression level of the gene coding for PPM1E protein, and/or a transcription product of the gene coding for PPM1E protein and/or a fragment, or derivative, or variant thereof.

In another aspect, the invention features a method for identifying agents for the treatment and/or prevention of neurodegenerative diseases, in particular AD, or related diseases and disorders. Said method comprises (a) contacting a neuronal cell which expresses a protein phosphatase 1 E or a fragment, or derivative, or variant thereof with an agent (b) determine the number of dendritic spines and/or dendritic spine density in said cell (c) comparing the number of dendritic spines and/or the dendritic spine density determined in step (b) with the number of dendritic spines and/or dendritic spine density in a cell which expresses a protein phosphatase 1 E or a fragment, or derivative, or variant thereof, not contacted with said agent, (d) identifying agents modulating the number of dendritic spines and/or dendritic spine density as agents for the treatment and/or prevention of neurodegenerative disorders.

In a preferred embodiment of said method of identifying or of testing agents for the treatment and/or prevention of neurodegenerative diseases said agents are identified or tested which increase the number of dendritic spines and/or dendritic spine density.

Said agents modulating the number of dendritic spines and/or dendritic spine density by modulating the enzymatic activity and/or binding capacity and/or expression and/or functionality of a protein phosphatase 1 E and/or a gene coding for a PPM1E protein, and/or a transcription product of the gene coding for a PPM1E protein and/or a fragment, or derivative, or variant thereof.

In a particular embodiment said neuronal cell which expresses a protein phosphatase 1 E or a fragment, or derivative, or variant thereof comprises an expression system for expression of PPM1E.

In a further particular embodiment said neuronal cell which expresses a protein phosphatase 1 E or a fragment, or derivative, or variant thereof overexpresses PPM1E.

Further, said cell may comprise an expression system for expression of a detection system, in particular a fluorescent protein.

Cells expressing or overexpressing a protein PPM1E and the use thereof are disclosed in Example 2 and 3.

It is preferred that in said methods of identifying or of testing agents for the treatment and/or prevention of neurodegenerative diseases the gene coding for a protein phosphatase 1 E is the gene coding for a protein phosphatase 1 E protein having SEQ ID NO:1 or SEQ ID NO: 2 and/or wherein a transcription product of the gene coding for PPM1E protein is the gene coding for a PPM1E protein having SEQ ID NO: 1 or SEQ ID NO: 2, and/or a fragment, or derivative, or variant thereof.

It is further preferred that said neurodegenerative disease is Alzheimer's disease.

In a further aspect the invention makes use of a cell, which cell comprises a nucleic acid comprising a PPM1E sequence coding for a PPM1E protein (preferably having SEQ ID NO: 1 or SEQ ID NO: 2), or a fragment, or derivative, or variant thereof. Said cell may comprise an expression system for expression of PPM1E. Said cell may mis-express, under-express, non-express or over-express, or express a disrupted or in another way altered PPM1E protein for identifying, testing, screening and validating agents, compounds, modulators in the development of diagnostics and therapeutics to treat and prevent neurodegenerative diseases, in particular Alzheimer's disease. In a preferred embodiment said cell is used in a method of identifying or testing agents according to the instant invention.

In one further aspect, the invention features methods of identifying, of testing and of screening agents and uses according to the instant invention, wherein said agents, test compounds are administered to a tissue or to a non-human animal which non-human animal is predisposed to developing or has already developed signs and symptoms of a neurodegenerative disease or related diseases or disorders, preferably symptoms related to symptoms of Alzheimer's disease.

In a further aspect, the present invention provides a method for identifying agents or for testing agents for the treatment or prevention of neurodegenerative diseases, which agents are binding to a gene coding for protein phosphatase 1 E, and/or a transcription product of the gene coding for protein phosphatase 1 E, and/or a translation product of the gene coding for protein phosphatase 1 E, and/or a fragment, or derivative, or variant thereof, or which agents modulating the binding between a substance and a gene coding for protein phosphatase 1 E, and/or a transcription product of the gene coding for protein phosphatase 1 E, and/or a translation product of the gene coding for protein phosphatase 1 E, and/or a fragment, or derivative, or variant thereof.

In a preferred embodiment of the method for identifying agents or for testing agents said agents modulating the binding between a substance and a gene coding for protein phosphatase 1 E, and/or a transcription product of the gene coding for protein phosphatase 1 E, and/or a translation product of the gene coding for protein phosphatase 1 E, and/or a fragment, or derivative, or variant thereof, are modulating the binding by inhibiting the binding or by enhancing the binding or by altering the degree of binding. It is further preferred that said gene coding for protein phosphatase 1 E is the gene coding for a protein phosphatase 1 E protein having SEQ ID NO:1 or SEQ ID NO: 2, and wherein said translation product of the gene coding for protein phosphatase 1 E proteins is the protein phosphatase 1 E protein having SEQ ID NO: 1 or SEQ ID NO: 2. It is further preferred that said neurodegenerative disease is Alzheimer's disease.

In another aspect, the present invention provides for a method of screening, for a method of identifying or testing agents, a compound or compounds, preferably for screening, identifying, testing a plurality of agents, compounds in high-throughput format, to determine the degree of inhibition of binding or the enhancement of binding between a substance, ligand and PPM1E protein (preferably having SEQ ID NO: 1 or SEQ ID NO: 2), or a fragment, or derivative, or variant thereof by an agent, a compound and/or to determine the degree of binding of said agents, compounds to PPM1E protein (preferably having SEQ ID NO: 1 or SEQ ID NO: 2), or a fragment, or derivative, or variant thereof. For determination of inhibition of binding between a substance, ligand and PPM1E protein, or a fragment, or derivative, or variant thereof, said method of screening, identifying, testing comprise the steps of (i) adding a liquid suspension of said PPM1E protein, or a fragment, or derivative, or variant thereof, to a plurality of containers, and (ii) adding an agent, compound or a plurality of agents, compounds to be screened, tested for said inhibition to said plurality of containers, and (iii) adding a detectable, preferably a fluorescently labelled substance, ligand to said containers, and (iv) incubating said PPM1E protein, or said fragment, or derivative or variant thereof, and said agent, compound or plurality of agents, compounds, and said detectable, preferably fluorescently labelled substance, ligand, and (v) measuring the amounts of substance, ligand, preferably its fluorescence, associated with said PPM1E protein, or with said fragment, or derivative, or variant thereof, and (vi) determining the degree of inhibition by one or more of said agents, compounds of binding of said substance, ligand to said PPM1E protein, or said fragment, or derivative, or variant thereof. It might be preferred to reconstitute said PPM1E translation product, or fragment, or derivative, or variant thereof into artificial liposomes to generate the corresponding proteoliposomes to determine the inhibition of binding between a substance, ligand and said PPM1E translation product. Methods of reconstitution of PPM1E translation products from detergent into liposomes have been detailed (Schwarz et al., *Biochemistry* 1999, 38: 9456-9464; Krivosheev and Usanov, *Biochemistry-Moscow* 1997, 62: 1064-1073). Instead of utilizing a fluorescently labelled substance, ligand, it might in some aspects be preferred to use any other detectable label known to the person skilled in the art, e.g. radioactive labels, and detect it accordingly. Said method may be useful for the identification of novel agents, compounds as well as for evaluating agents, compounds which have been improved or otherwise optimized in their ability to inhibit the binding of a substance, ligand to a gene product of the gene coding for PPM1E protein, or a fragment, or derivative, or variant thereof. One example of a fluorescent binding assay, in this case based on the use of carrier particles, is disclosed and described in patent application WO00/52451. A further example is the competitive assay method as described in patent WO02/01226. Preferred signal detection methods for screening assays of the instant invention are described in the following patent applications: WO96/13744, WO98/16814, WO99/34195, WO00/66985, and WO01/59416.

Furthermore, the present invention provides for a method of screening, for a method of identifying or testing agents, a compound or compounds, preferably for screening, identifying, testing a plurality of agents, compounds in high-throughput format, to determine the degree of binding of said agents, compounds to PPM1E protein (preferably having SEQ ID NO: 1 or SEQ ID NO: 2), or to a fragment, or derivative, or variant thereof, said method of screening, identifying or testing comprises (i) adding a liquid suspension of said PPM1E protein, or a fragment, or derivative, or variant thereof, to a plurality of containers, and (ii) adding a detectable, preferably a fluorescently labelled agent, compound or a plurality of detectable, preferably fluorescently labelled agents, compounds to be screened for said binding to said plurality of containers, and (iii) incubating said PPM1E protein, or said fragment, or derivative, or variant thereof, and said detectable, preferably fluorescently labelled agent, compound or detectable, preferably fluorescently labelled agents, compounds, and (iv) measuring the amounts of agent, compound, preferably its fluorescence, associated with said PPM1E protein, or with said fragment, or derivative, or variant thereof, and (v) determining the degree of binding by one or more of said agents, compounds to said PPM1E protein, or said fragment, or derivative, or variant thereof. In this type of screening method, assay it might be preferred to use a fluorescent label. However, any other type of detectable label might also be employed. Also in this type of assay it might be preferred to reconstitute a PPM1E translation product or a fragment, or derivative, or variant thereof into artificial liposomes as described in the present invention. Said assay methods may be useful for the identification of novel agents, compounds as well as for testing, evaluating agents, compounds which have been improved or otherwise optimized in their ability to bind to PPM1E protein, or a fragment, or derivative, or variant thereof.

In another aspect, the invention features a method of treating or preventing a neurodegenerative disease, in particular AD, in a subject comprising the administration to said subject in need of such a treatment in a therapeutically or prophylactically effective amount and formulation an agent, modulating agents, modulators, compounds, antagonist, agonists or antibodies which directly or indirectly affect a level and/or an activity, an expression level and/or enzymatic activity, of (i) the gene coding for PPM1E proteins, and/or (ii) a transcription product of the gene coding for PPM1E proteins, and/or (iii) a translation product of the gene coding for PPM1E proteins, and/or (iv) a fragment, or derivative, or variant of (i) to (iii). Said agent, compound may comprise a small molecule, or it may also comprise a peptide, an oligopeptide, or a polypeptide. Said peptide, oligopeptide, or polypeptide may comprise an amino acid sequence of a translation product of the gene coding for PPM1E proteins, or a fragment, or derivative, or a variant thereof. An agent for treating or preventing a neurodegenerative disease, in particular AD, according to the instant invention, may also consist of a nucleotide, an oligonucleotide, or a polynucleotide. Said oligonucleotide or polynucleotide may comprise a nucleotide sequence of the gene coding for PPM1E proteins, either in sense orientation or in antisense orientation.

In another aspect, the invention provides for the use of an agent, an antibody, an antagonist or agonist, or a modulator of an activity and/or a level, an enzymatic activity and/or expression level of (i) the gene coding for PPM1E proteins, and/or (ii) a transcription product of the gene coding for PPM1E proteins, and/or (iii) a translation product of the gene coding for PPM1E proteins, and/or (iv) a fragment, or derivative, or variant of (i) to (iii) in the manufacture of a medicament for treating or preventing a neurodegenerative disease, in particular AD. Said antibody may be specifically immunoreactive with an immunogen which is a translation product of a gene coding for PPM1E (preferably having SEQ ID NO: 1 or SEQ ID NO: 2) or a fragment, derivative or variant of such translation product.

In general, the aforementioned screening methods, methods of identifying, testing, assays as well as potential drug molecules (e.g. agents, compounds, modulators, antagonists, agonists) identified thereof have applicability in relation to the treatment or prevention of neurodegenerative diseases, in particular Alzheimer's disease.

Another aspect of the present invention features protein molecules being translation products of the gene coding for PPM1E and the use of said protein molecules (preferably having SEQ ID NO: 1 or SEQ ID NO: 2), or fragments, or derivatives, or variants thereof, as diagnostic targets for detecting a neurodegenerative disease, in particular Alzheimer's disease.

The present invention further features protein molecules being translation products of the gene coding for PPM1E and the use of said protein molecules (preferably having SEQ ID NO: 1 or SEQ ID NO: 2), or fragments, or derivatives, or variants thereof, as screening targets for agents, modulators, antagonists, agonists, reagents or compounds preventing, or treating, or ameliorating a neurodegenerative disease, in particular Alzheimer's disease.

The present invention features antibodies which are specifically immunoreactive with an immunogen, wherein said immunogen is a translation product of the PPM1E gene coding for PPM1E proteins (preferably having SEQ ID NO: 1 or SEQ ID NO: 2), or fragments, or derivatives, or variants thereof. The immunogen may comprise immunogenic or antigenic epitopes or portions of a translation product of said gene, wherein said immunogenic or antigenic portion of a translation product is a polypeptide, and wherein said polypeptide elicits an antibody response in an animal, and wherein said polypeptide is immunospecifically bound by said antibody. Methods for generating antibodies are well known in the art (see Harlow et al., *Antibodies, A Laboratory Manual*, Cold Spring Harbor Laboratory Press, Cold Spring Harbor, N.Y., 1988). The term "antibody", as employed in the present invention, encompasses all forms of antibodies known in the art, such as polyclonal, monoclonal, chimeric, recombinatorial, anti-idiotypic, humanized, or single chain antibodies, as well as fragments thereof (see Dubel and Breitling, *Recombinant Antibodies*, Wiley-Liss, New York, N.Y., 1999). Antibodies of the present invention are useful, for instance, in a variety of diagnostic and therapeutic methods, based on state-in-the-art techniques (see Harlow and Lane, *Using Antibodies: A Laboratory Manual*, Cold Spring Harbor Laboratory Press, Cold Spring Harbor, N.Y., 1999 and Edwards R., *Immunodiagnostics: A Practical Approach*, Oxford University Press, Oxford, England, 1999) such as enzyme-immunoassays (e.g. enzyme-linked immunosorbent assay, ELISA), radioimmunoassays, chemoluminescence-immunoassays, Western-blot, immunoprecipitation and antibody microarrays. These methods involve the detection of translation products of the PPM1E gene, or fragments, or derivatives, or variants thereof.

In a preferred embodiment of the present invention, said antibodies can be used for detecting the pathological state of a cell in a sample obtained from a subject, comprising immunocytochemical staining of said cell with said antibody, wherein an altered degree of staining, or an altered staining pattern in said cell compared to a cell representing a known health status indicates a pathological state of said cell. Preferably, the pathological state relates to a neurodegenerative disease, in particular to AD. Immunocytochemical staining of a cell can be carried out by a number of different experimental methods well known in the art. It might be preferred, however, to apply an automated method for the detection of antibody binding, wherein the determination of the degree of staining of a cell, or the determination of the cellular or subcellular staining pattern of a cell, or the topological distribution of an antigen on the cell surface or among organelles and other subcellular structures within the cell, are carried out according to the method described in U.S. Pat. No. 6,150,173.

Features and advantages of the invention will be apparent from the following description of figures and examples, which are illustrative only and not intended to limit the remainder of the disclosure in any way.

DESCRIPTION OF THE FIGURES

FIG. 1A: The table lists the data of differences in the levels of PPM1E gene derived mRNA in human brain tissue samples from individuals corresponding to different Braak stages indicative for AD as measured by quantitative RT-PCR analysis. It indicates that the levels of the respective mRNA species correlate quantitatively with AD progression and thus are indicative for AD as measured by the neuropathological staging of brain tissue samples according to Braak and Braak (Braak staging). cDNA probes of frontal cortex as well as of inferior temporal cortex each of 5 different donors with Braak stage 0 (C011, C012, C026, C027, and C032), 7 different donors with Braak stage 1 (C014, C028, C029, C030, C036, C038, and C039), 5 different donors with Braak stage 2 (C008, C031, C033, C034, and DE03), 4 different donors with Braak stage 3 (C025, DE07, DE11, and C057), and 3 different donors with Braak stage 4 (P012, P047, and P068) have been applied to an analysis by quantitative RT-PCR using the Roche Lightcycler rapid thermal cycling technique. The data were normalized to values of cyclophilin B a standard gene that showed no significant differences in its gene expression levels. The comparison between samples of the lowest Braak stage 0 with samples representing Braak stages 1, 2 and 3 clearly demonstrates a substantial difference in gene expression level of PPM1E (see also FIG. 1B). Further, comparing Braak stage 0 with Braak stages 1 and 2 indicates that differences of expression levels start already in very early Braak stages.

FIG. 1B: The graph demonstrates a substantial difference in gene expression level of PPM1E by comparison between samples of frontal (F) and inferior temporal cortex (T) representing different Braak stages.

Figure 2:
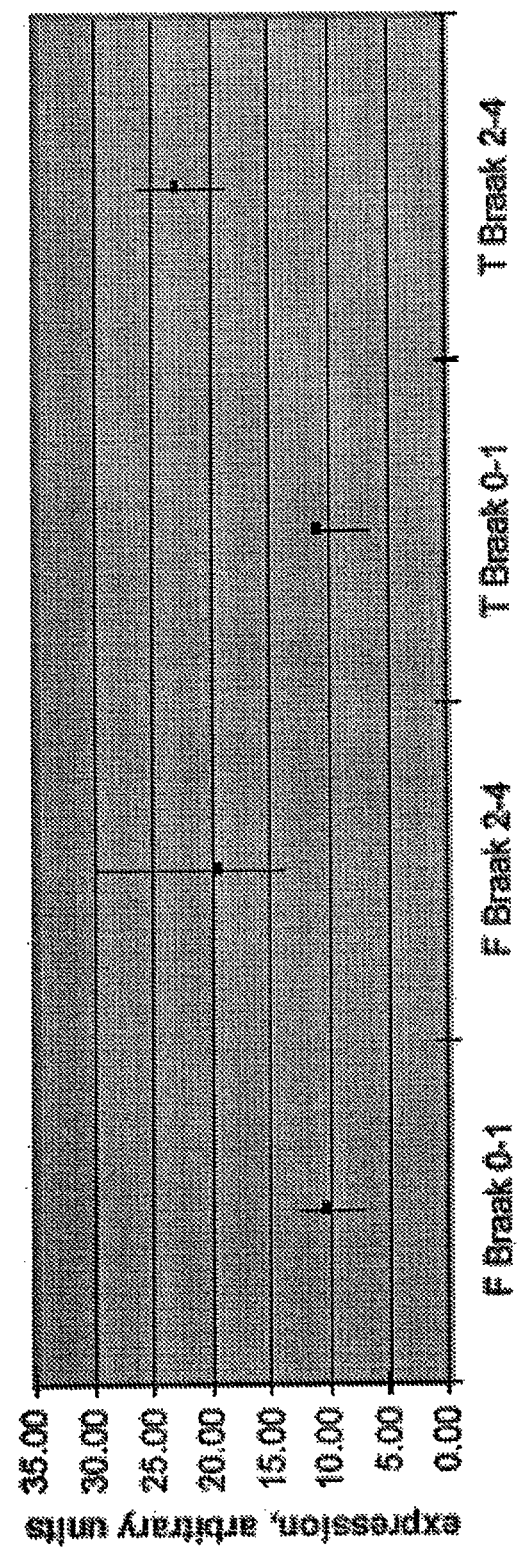
FIG. 2 shows the analysis of absolute levels of PPM1E gene derived mRNA in human brain tissue samples from individuals corresponding to different Braak stages indicative for AD as measured by quantitative RT-PCR and using statistical method of the median at 98%-confidence level.

FIG. 2: The graph shows the analysis of absolute levels of PPM1E gene derived mRNA in human brain tissue samples from individuals corresponding to different Braak stages indicative for AD as measured by quantitative RT-PCR and using statistical method of the median at 98%-confidence level (Sachs L (1988) Statistische Methoden: Planung and Auswertung. Heidelberg New York, p. 60). The data were calculated by defining control groups including subjects with Braak stages 0 to 1, which are compared with the data calculated for the defined groups with advanced AD pathology including Braak stages 2 to 4. A significant difference reflecting an up-regulation of PPM1E is shown comparing frontal (F) as well as inferior temporal cortices (T) of Braak stage 0-1 with Braak stage 2-4 in frontal as well as inferior temporal cortices. Said difference reflects an up-regulation of PPM1E in the frontal cortex as well as in the inferior temporal cortex of individuals with early AD pathology relative to the frontal cortex as well as to the inferior temporal cortex of control persons.

FIG. 3A: SEQ ID NO: 1, the amino acid sequence of the human PPM1E protein (full length form, variant or derivative or fragment no. 1) (RefSeq primary accession number NP_055721, Ensembl primary accession number ENSP00000312411) comprising 775 amino acids is shown.

FIG. 3B: SEQ ID NO: 2, the amino acid sequence of the human PPM1E protein (posttranslationally truncated form, variant or derivative or fragment no. 2 of SEQ ID NO: 1) comprising 557 amino acids is shown.

FIG. 4: SEQ ID NO: 3, the nucleotide sequence of the human PPM1E cDNA (Ensembl transcript ID number ENST00000308249) encoding the PPM1E protein, comprising 6535 nucleotides is shown.

FIG. 5: SEQ ID NO: 4, the nucleotide coding sequence (cds) of the human PPM1E cDNA (full length form) encoding the PPM1E full length protein, comprising 2268 nucleotides is shown.

Figures 6, 7:
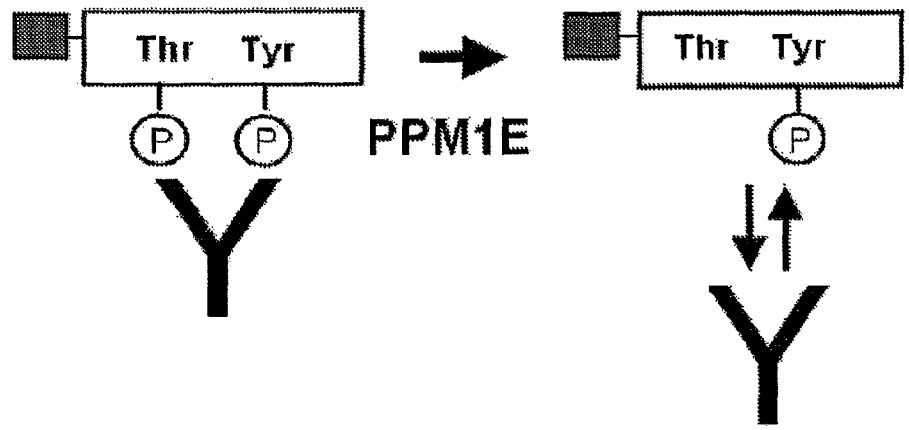
FIG. 6 depicts the sequence alignment of the primers used for PPM1E transcription level profiling by quantitative RT-PCR with the corresponding clippings of PPM1E coding sequence.
FIG. 7 shows the principle of a direct phosphatase assay.

FIG. 6: The sequence alignment of the primers used for PPM1E transcription level profiling (primer A, SEQ ID NO: 5 and primer B, SEQ ID NO: 6) by quantitative RT-PCR with the corresponding clippings of SEQ ID NO: 4, PPM1E coding cDNA sequence is shown.

FIG. 7: The schematic drawing depicts the principle of a direct phosphatase assay. The TAMRA-phosphopeptide (TAMRA substrate peptide) becomes dephosphorylated at the threonine residue (Thr) in the presence of the phosphoserine/threonine phosphatase PPM1E (p means phosphorylated). Besides the threonine residue (Thr) also the tyrosine residue (Tyr) in this substrate peptide is phosphorylated ($\hat{P}$). Upon dephosphorylation of the phosphothreonine residue by the phosphatase activity of PPM1E, the fluorescently TAMRA-labelled substrate peptide will no more bind to the polyclonal anti-active JNK antibody. As a results, a drop of the fluorescence polarization is detected which is inversely proportional to phosphatase activity.

Figure 8:
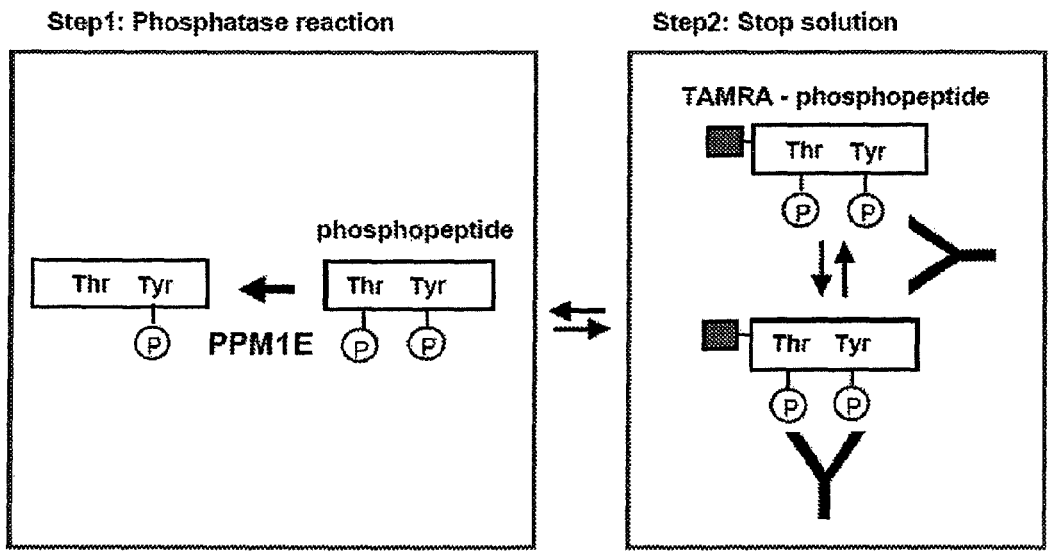
FIG. 8 shows the principle of an indirect phosphatase assay.

FIG. 8: The schematic drawing shows the principle of an indirect phosphatase assay. In a first step, the bis-phosphorylated non-fluorescent phosphopeptide (substrate peptide) is dephosphorylated by the activity of the phosphatase PPM1E. The product of the reaction (mono-phosphorylated substrate peptide) will no more compete with the TAMRA-labelled substrate peptide for the binding to the polyclonal anti-active JNK antibody which are both added in a second step (stop solution including a reagent inactivating the phosphatase).

Figure 9:
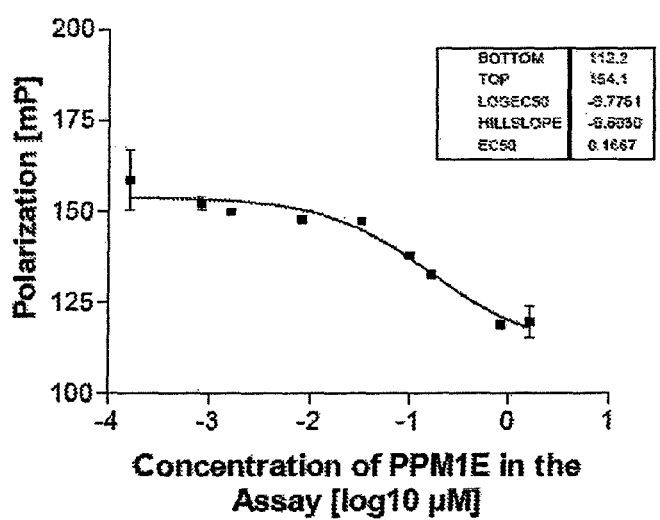
FIG. 9 shows a titration experiment of PPM1E phosphatase reaction using the TAMRA substrate peptide and polyclonal anti-active JNK antibody.

FIG. 9: The graph shows a titration experiment of PPM1E phosphatase reaction using the 5-TAMRA-MpTPpYV-NH2 substrate peptide and polyclonal anti-active JNK antibody which binds to the bis-phosphorylated substrate peptide, but not after dephosphorylation. The curve indicates a loss of antibody binding to the substrate peptide (decrease of polarization) with increasing level of PPM1E phosphatase concentration. At a concentration of PPM1E of 33 nM (log 10=−1.5) of the PPM1E protein stock solution (2.8 µg/ml, 33 µM) a polarization of about 147 mP (milli-Polarization) was measured, whereas at a concentration of 0.8 µM (log 10=−0.078) of the PPM1E protein stock solution the polarization decreased to about 123 mP. The IC50 (EC50) value was reached at a concentration of 0.16 µM of the PPM1E protein stock solution. The titration experiment is further described in detail in Example 2 (i).

Figure 10:
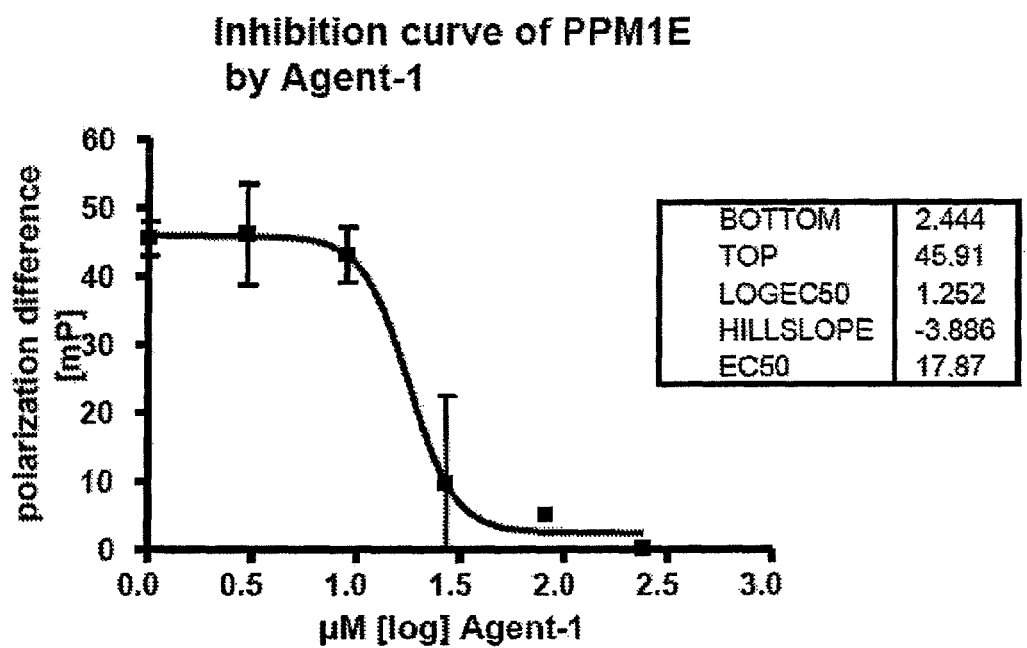
FIG. 10 shows the inhibition of the PPM1E phosphatase-dependent dephosphorylation of the TAMRA substrate peptide by the agent-1.

FIG. 10: The graph shows the inhibition of the PPM1E phosphatase-dependent dephosphorylation of the TAMRA substrate peptide by the agent-1. The titration experiment was performed using a constant concentration of His-PPM1E phosphatase. The graph depicts the change in polarisation difference (mP) with rising concentration of the agent-1 (µM [log]). Polarisation difference is calculated as the maximal polarisation minus the actual polarisation at the corresponding agent-1 concentration. With increasing agent-1 concentration the polarisation rises in consequence of an inhibition of the PPM1E phosphatase activity, a loss of PPM1E phosphatase activity, which leads to an increase in binding of the anti-active JNK antibody to the TAMRA substrate peptide.

Figure 11:
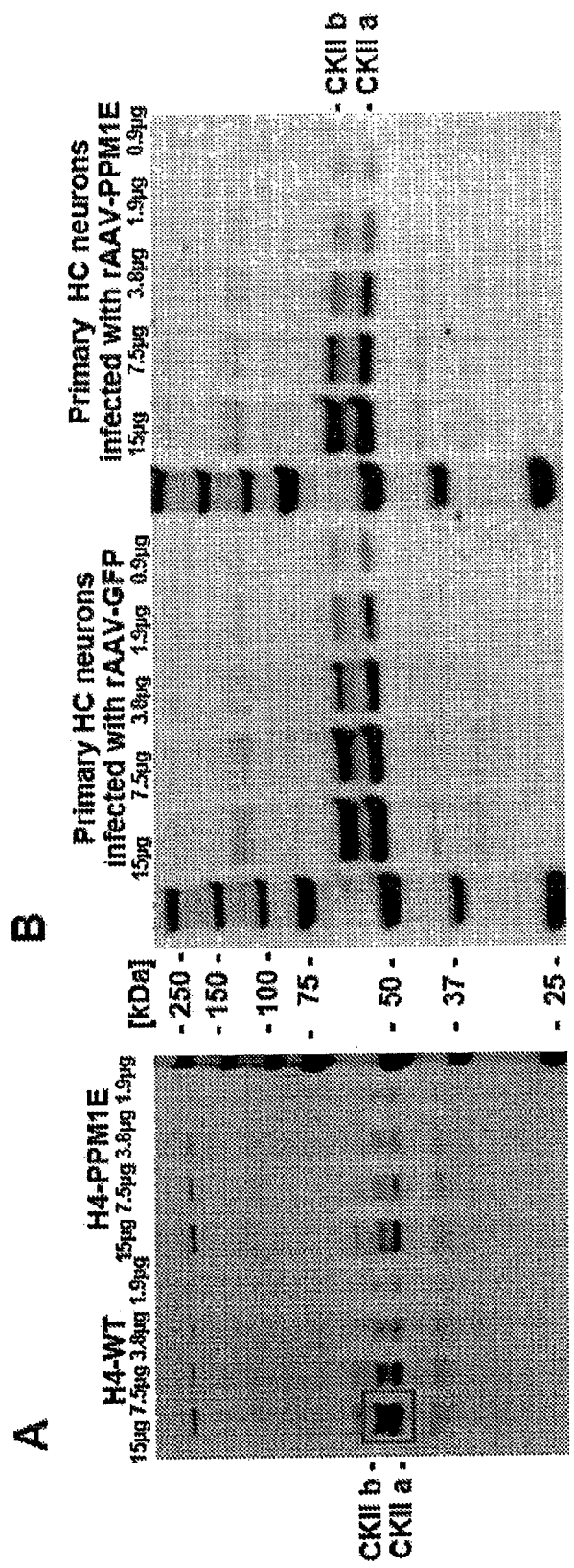
FIG. 11 shows western blots with dilution series of PPM1E overexpressing and wildtype neuronal cells.

FIG. 11: The figures show western blots with dilution series (0.9 µg to 15 µg total protein extract loaded) of PPM1E overexpressing and wildtype neuronal cells. Phosphorylation of the substrate Ca2+/calmodulin-dependent protein kinase (CaMKII) by PPM1E was detected with a phosphorylation-specific antibody (antibody ab32678 (Abcam)) which detects phosphorylated threonine at amino acid position 286 (p286) of the CaMKII kinase. PPM1E has been overexpressed in H4 neuroglioma cell lines (H4-PPM1E) (FIG. 11 A) which were compared with H4 wildtype cells (H4-WT). FIG. 11 B shows the overexpression of PPM1E in hippocampal rat primary neuronal cell culture (HC neurons) compared to hippocampal rat primary neuronal cell culture expressing only GFP (green fluorescent protein) (negative control). The level of overexpression of PPM1E ranged from about 50× in a stable H4 cell line to about 10× in with rAA-PPM1E virus infected primary neuronal cells.

The overexpression and the activity of PPM1E was indirectly detected by the phosphorylation status of the target protein CaMKII (Ca2+/calmodulin-dependent protein kinase). The quantification was performed by western blotting with the ECF or Qdot detection systems (Invitrogen). The isoform CaMKII beta (CKII b) with about 57 kDa and the isoform CaMKII alpha (CKII a) with about 50 kDa are both detected by the phosphorylation-specific antibody ab32678 (Abcam). Generally, the phosphorylation of both isoforms has been quantified together as shown in FIG. 11A (highlighted by a box) and FIG. 11B. The data were normalized to beta-Actin. More details are described in Example 3 (i) and (ii). Comparison of the bands of wildtype cells or cells not infected with PPM1E (H4-WT, HC neurons rAAV-GFP) with those of the PPM1E overexpressing cells (H4-PPM1E, HC neurons rAAV-PPM1E) at the same concentration of loaded cell extracts (either 15 µg, 7.5 µg, 3.8 µg, 1.9 µg, or 0.9 µg) shows a weaker phosphorylation status of CaMKII alpha and CaMKII beta in PPM1E overexpressing cells. This difference in signal intensity reflects the dephosphorylation activity of the PPM1E phosphatase, dephosphorylating CaMKII alpha and beta at Thr286.

Figure 12:
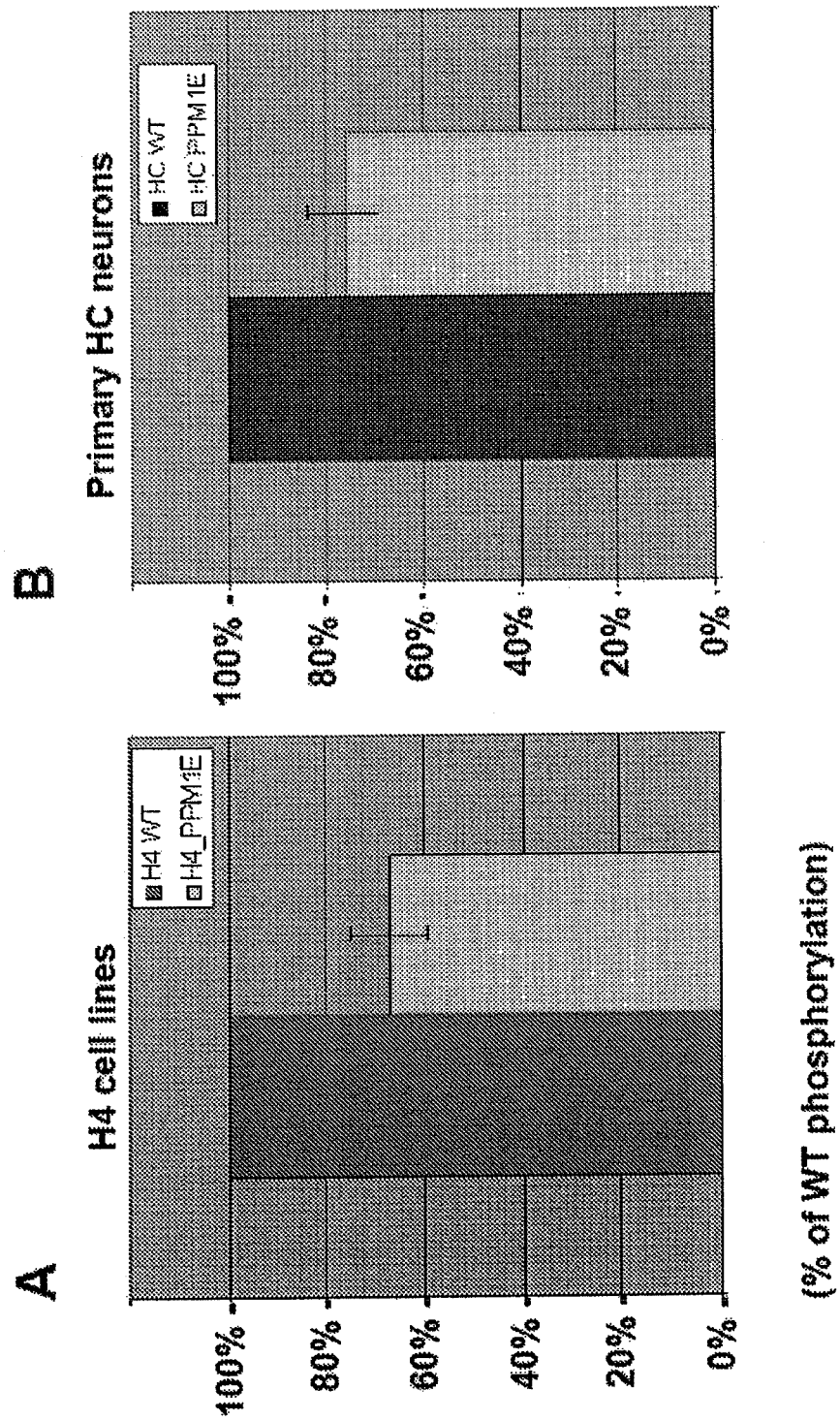
FIG. 12 schematically shows the evaluation of the western blots depicted in FIG. 11 and thereby the activity of overexpressed PPM1E in neuronal H4 cells and in primary HC neurons.

FIG. 12: The diagram schematically shows the evaluation of the western blots depicted in FIG. 11 and thereby the activity of overexpressed PPM1E in neuronal H4 cells (FIG. 11 A) and in primary HC neurons (FIG. 11 B). The phosphorylation status of CaMKII (CaMKII alpha and CaMKII beta) is reduced due to PPM1E overexpression (bars of H4_PPM1E and HC PPM1E) compared to wildtype (WT), verifying that the phosphatase is active in H4 cells (FIG. 11 A) as well as in primary HC neurons (FIG. 11 B). Wildtype phosphorylation was set to 100%. Mean values were calculated from the different cell extract concentration on the western blot after setting them in a relative context to the corresponding WT-value.

FIG. 13: The diagram shows a separate evaluation of the pCaMKII alpha and pCaMKII beta (p=phosphorylated) bands of the western blots shown in FIG. 11. All values for the different cell extract concentrations (15 µg, 7.5 µg, 3.8 µg, 1.9 µg, or 0.9 µg) on the western blots are shown in separated curves.

The curves indicate that PPM1E phosphatase is dephosphorylating the beta isoform (57 kDa) as well as the alpha isoform (50 kDa) of CaMKII. Independent data with PPM1E overexpressing hippocampal rat primary neurons (PPM1E HC neurons) (FIG. 13 A) and PPM1E overexpressing H4 cells (H4 PPM1E) (FIG. 13 B) indicate that the reduction of CaMKII phosphorylation (pCaMKII) depends on level of PPM1E expression (see also FIG. 11). Details are described in Example 3 (i) and (ii).

Figure 14:
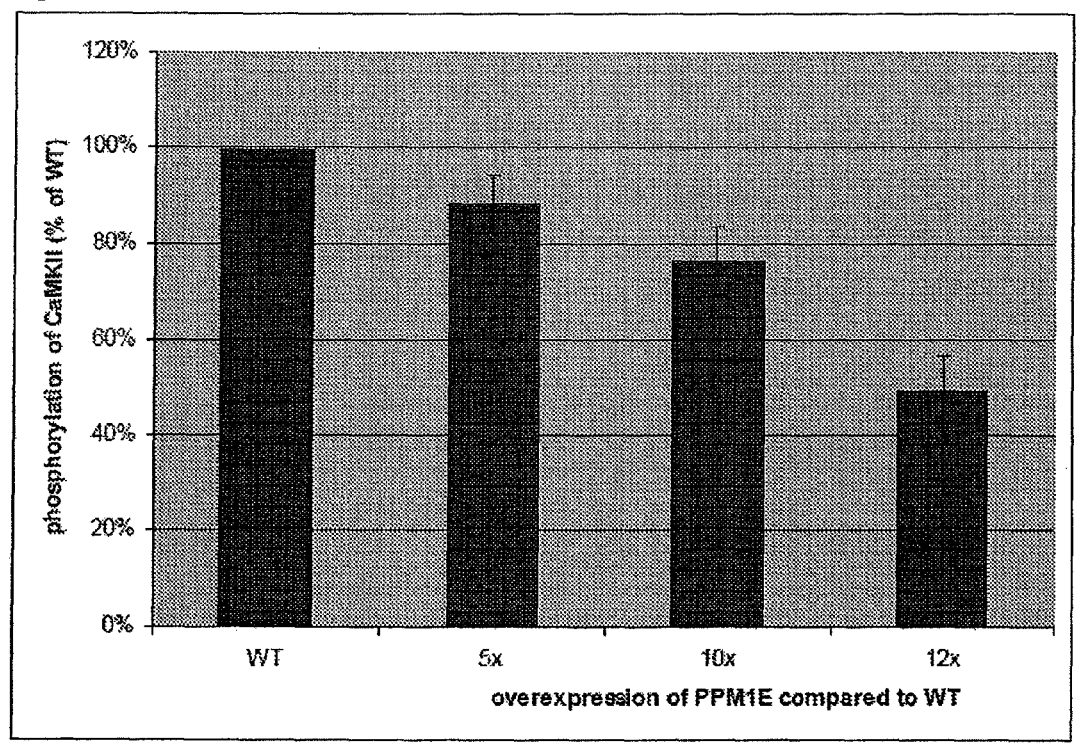
FIG. 14 schematically shows that phosphorylation of CaMKII (alpha and beta isoform of CaMKII) is inversely correlated with the level of PPM1E overexpression.

FIG. 14: The diagram shows that phosphorylation of CaMKII (alpha and beta isoform of CaMKII) is inversely correlated with the level of PPM1E overexpression. Setting all WT values to 100% the inverse correlation become apparent. The data of the western blot quantification of protein expression levels and phosphorylation status (FIG. 11B) were used.

Comparing PPM1E overexpressing HC neurons with wildtype HC neurons, the phosphorylation of CaMKII is decreasing to 50% of the phosphorylation status of wildtype cells by increasing the level of PPM1E expression 12 times which is indicative for a reduction of CaMKII phosphorylation by PPM1E phosphatase.

Figure 15:
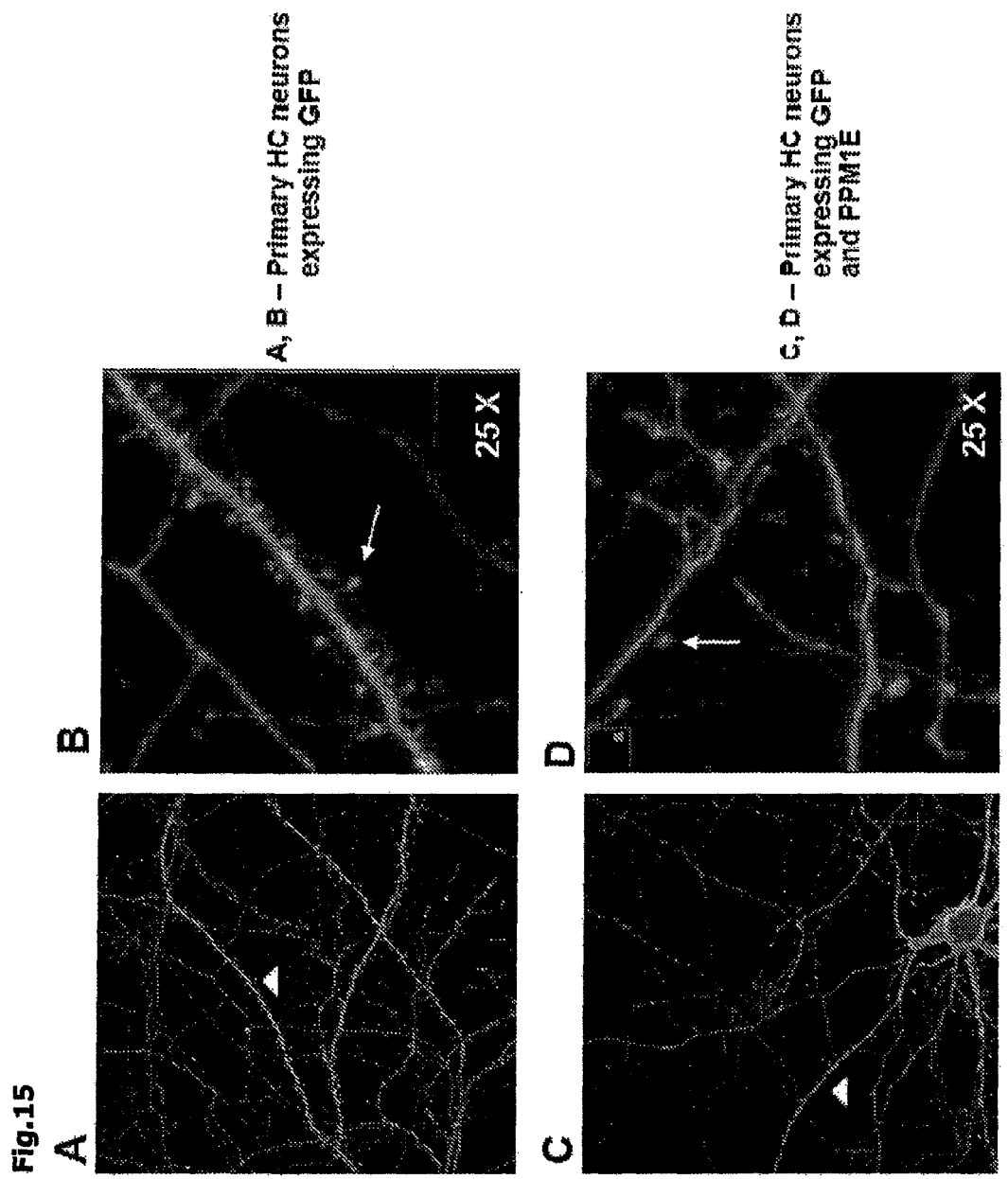
FIG. 15 shows confocal stacks of dendritic spines along secondary dendrites of HC neurons expressing GFP only and PPM1E HC neurons expressing GFP and PPM1E phosphatase.

FIG. 15: The pictures show HC neurons expressing GFP (green fluorescent protein) only (controls) (FIG. 15 A and FIG. 15 B, 25× magnified) and PPM1E HC neurons expressing GFP and PPM1E phosphatase (FIG. 15 C and FIG. 15 D, 25× magnified). The number of dendritic spines (one dendritic spine as example is indicated by an arrow) along the secondary dendrites (indicated by a triangle) of control HC neurons and those of PPM1E HC neurons, expressing PPM1E phosphatase and GFP, were counted. The number of spines is markedly reduced in the PPM1E HC neurons (FIG. 15 C, D) which indicates that PPM1E impairs synaptic integrity and function in HC neurons and thus, plays a role in neurodegeneration of neurological disorders. The pictures (confocal stacks) were taken at 63× magnification and 2× zoom. The enlarged pictures of FIG. 15 B, D were taken at a 25× zoom of the pictures FIG. 15 A, B. More details are described in Example 3 (iii).

Figure 16:
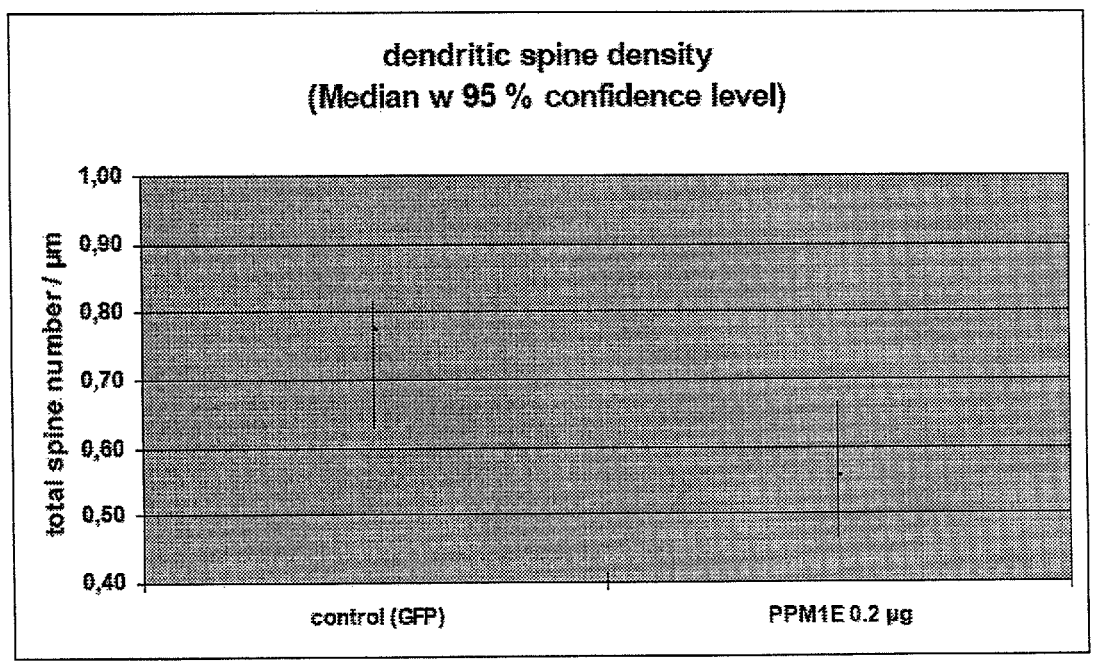
FIG. 16 schematically shows the reduction of the number of dendritic spines, of dendritic spine density of HC neurons expressing GFP only and of PPM1E HC neurons expressing GFP and PPM1E phosphatase.

FIG. 16: The reduction of the number of dendritic spines, of dendritic spine density as shown in FIG. 15 is presented by a diagram. Dendritic spines along secondary dendrites of confocal stacks of 30 PPM1E HC neurons and of 30 wildtype HC neurons were counted at a maximal resolution (n=30, three independent experiments). The number of dendritic spines is reduced by about 30% in PPM1E expressing HC neurons compared to HC neurons expressing GFP only. The difference was calculated by the Student's T-test and additionally by calculating the median as well as the 95%-confidence level (Sachs L (1988) Statistische Methoden Planung and Auswertung. Heidelberg New York). More details are described in Example 3 (iii).

EXAMPLES

Example 1

Differential Expression of PPM1E Gene in Human Brain Tissue Samples

In order to identify specific differences in the expression of genes that are associated with AD, real-time quantitative PCR (qPCR) analyses were performed with a diversity of mRNAs derived from human brain tissue specimens from clinically and neuropathologically well characterized individuals. Verification of the differential expression of individual genes was performed applying qPCR using gene-specific oligonucleotides. This technique is widely used to generate expression profiles of multiple genes and to compare populations of mRNA present in different tissue samples. In the present invention, mRNA populations present in selected post-mortem brain tissue specimens (frontal and inferior temporal cortex) were analyzed. Tissue samples were derived from individuals that could be grouped into different Braak stages reflecting the full range between healthy control individuals (Braak 0) and individuals that suffered from AD signs and symptoms (Braak 4). The methods were designed to specifically detect differences of expression levels at early Braak stages, which is indicative for pathological events occurring early in the course of the disease. Thus, said genes identified to be differential are effectively implicated in the pathogenesis of AD.

(i) Brain Tissue Dissection from Patients with AD:

Brain tissues from AD patients and age-matched control subjects, were collected. Within 6 hours post-mortem time the samples were immediately frozen on dry ice. Sample sections from each tissue were fixed in paraformaldehyde and neuropathologically staged at various stages of neurofibrillary pathology according to Braak and Braak into Braak stages (0-4). Brain areas for differential expression analysis were identified and stored at −80° C. until RNA extractions were performed.

(ii) Isolation of Total mRNA:

Total RNA was extracted from frozen post-mortem brain tissue by using the RNeasy kit (Qiagen) according to the manufacturer's protocol. The accurate RNA concentration and the RNA quality were determined applying the Eukaryote total RNA Nano LabChip system by using the 2100 Bioanalyzer (Agilent Technologies). For additional quality testing of the prepared RNA, i.e. exclusion of partial degradation and testing for DNA contamination, specifically designed intronic GAPDH oligonucleotides and genomic DNA as reference control were utilised to generate a melting curve with the LightCycler technology (Roche) as described in the supplied protocol by the manufacturer.

(iii) Quantitative RT-PCR:

Identification and positive corroboration of differential PPM1E gene expression was performed using the LightCycler technology (Roche). This technique features rapid thermal cycling for the polymerase chain reaction as well as real-time measurement of fluorescent signals during amplification and therefore allows for highly accurate quantification of RT-PCR products by using a kinetic, rather than endpoint readout. The relative quantity of PPM1E cDNAs from the frontal and temporal cortices of AD patients and age-matched control individuals respectively, were determined in a number of four up to nine tissues per Braak stage.

First, a standard curve was generated to determine the efficiency of the PCR with specific primers for the gene coding for PPM1E: Primer A, SEQ ID NO: 5, 5'-GTTCTG- GATGGGACCGAAGA-3' (nucleotides 1264-1283 of SEQ ID NO: 4) and Primer B, SEQ ID NO: 6, 3'-AAAGTTGT-GTCCGACCACCTG-5' (nucleotides 1342-1362 of SEQ ID NO: 4). PCR amplification (95° C. and 1 sec, 56° C. and 5 sec, and 72° C. and 5 sec) was performed in a volume of 20 µl containing LightCycler-FastStart DNA Master SYBR Green I mix (contains FastStart Taq DNA polymerase, reaction buffer, dNTP mix with dUTP instead of dTTP, SYBR Green I dye, and 1 mM MgCl2; Roche), 0.5 µM primers, 2 µl of a cDNA dilution series (final concentration of 40, 20, 10, 5, 1 and 0.5 ng human total brain cDNA; Clontech) and additional 3 mM MgCl2. Melting curve analysis revealed a single peak at approximately 86° C. with no visible primer dimers. Quality and size of the qPCR product were determined applying the DNA 500 LabChip system using the 2100 Bioanalyzer (Agilent Technologies). A single peak at the expected size of 99 bp for the gene coding for PPM1E protein was observed in the electropherogram of the sample. In an analogous manner, the qPCR protocol was applied to determine the PCR efficiency of cyclophilin B, using the specific primers SEQ ID NO: 7, 5'-ACTGAAGCACTACGGGCCTG-3' and SEQ ID NO: 8, 5'-AGCCGTTGGTGTCTTTGCC-3' except for MgCl2 (an additional 1 mM was added instead of 3 mM). Melting curve analysis revealed a single peak at approximately 87° C. with no visible primer dimers. Bioanalyzer analysis of the PCR product showed one single peak of the expected size (62 bp).

For calculation of the standard values, first the logarithm of the used cDNA concentration was plotted against the threshold cycle value Ct for PPM1E and Cyclophilin B respectively. The slopes and the intercepts of the standard curves (i.e. linear regressions) were calculated. In a second step, mRNA expression from frontal and inferior temporal cortices of controls and AD patients were analyzed in parallel. The Ct values were measured and converted to ng total brain cDNA using the corresponding standard curves:

$$10^{(Ct\ value - intercept)/slope}[ng\ total\ brain\ cDNA]$$

Calculated cDNA concentration values were normalized to Cyclophilin B that was analyzed in parallel for each tested tissue probe, thus resulting values are defined as arbitrary relative expression levels. The results of such quantitative RT-PCR analysis for the gene coding for PPM1E protein are shown in FIG. 1A and FIG. 1B.

(iv) Statistical Analysis of the mRNA Expression Comparing Donor Groups with Different Braak Stages.

For this analysis it was proven that absolute values of real-time quantitative PCR (Lightcycler method) between different experiments at different time points are consistent enough to be used for quantitative comparisons without usage of calibrators. Cyclophilin was used as a standard for normalization in any of the qPCR experiments for more than 100 tissues. Between others it was found to be the most consistently expressed housekeeping gene in the normalization experiments. Therefore a proof of concept was done by using values that were generated for cyclophilin.

First analysis used cyclophilin values from qPCR experiments of frontal cortex and inferior temporal cortex tissues from three different donors. From each tissue the same cDNA preparation was used in all analyzed experiments. Within this analysis no normal distribution of values was achieved due to small number of data. Therefore the method of median and its 98%-confidence level was applied (Sachs L (1988) Statistische Methoden: Planung und Auswertung. Heidelberg New York, p. 60). This analysis revealed a middle deviation of 8.7% from the median for comparison of absolute values and a middle deviation of 6.6% from the median for relative comparison.

Second analysis used cyclophilin values from qPCR experiments of frontal cortex and inferior temporal cortex tissues from two different donors each, but different cDNA preparations from different time points were used. This analysis revealed a middle deviation of 29.2% from the median for comparison of absolute values and a middle deviation of 17.6% from the median for relative comparison. From this analysis it was concluded, that absolute values from qPCR experiments can be used, but the middle deviation from median should be taken into further considerations.

A detailed analysis of absolute values for PPM1E was performed using the method of median and its 98%-confidence level. Because in contrast to the mean the calculation of the median is not affected by single data outliers; therefore latter is the method of choice for a small number of data that are distributed non-normal and/or assymetric (Sachs L (1988) Statistische Methoden: Planung und Auswertung. Heidelberg New York, p. 60). Therefore, absolute levels of PPM1E were used after relative normalization with cyclophilin. The median as well as the 98%-confidence level was calculated for a group consisting of low level Braak stages (Braak 0-Braak 1) and the group consisting of high level Braak stages (Braak 2-Braak 4). The analysis was aimed to identify early onset of mRNA expression differences within the course of AD pathology. Said analysis described above is shown in FIG. 2.

Example 2

Assay Development

General Example 2A

General Description of the Direct Phosphatase Assay

The assay is based on the dephosphorylation of the substrate peptide 5-TAMRA-MpTPpYV-NH$_2$ (TAMRA-phosphopeptide) by the phosphoserine/threonine phosphatase PPM1E. Besides the threonine residue (Thr) also the tyrosine residue (Tyr) in this peptide is phosphorylated (Ⓟ). The polyclonal anti-active JNK antibody binds to the dually phosphorylated fluorescently labelled substrate peptide. After dephosphorylation of the phosphothreonine residue by the phosphatase activity of PPM1E the antibody no longer binds to the formed desphosphorylated substrate peptide product. The decreased binding of the antibody to the peptide substrate can be measured by a decrease in fluorescence polarization using 2D-FIDA anisotropy. The fluorescence polarization detected is inversely proportional to PPM1E phosphatase activity. The principle of the direct phosphatase assay using PPM1E phosphatase is shown in FIG. 7.

General Example 2B

General Description of the Indirect Phosphatase Assay

The assay is based on the dephosphorylation of non-fluorescent substrate peptide by PPM1E phosphatase.

PPM1E phosphatase is incubated with bisphosphorylated substrate peptide (non-labelled) in a total volume of 80 µl reaction buffer at 30° C. In a second step, at different time points, aliquots (20 µl) are withdrawn from the enzyme reaction and are mixed with 10 µl of the STOP solution containing hydrogen peroxide, TAMRA substrate peptide together with the polyclonal antiactive JNK antibody. As a result of the PPM1E activity, the substrate peptide is dephosphorylated and does no longer compete with the TAMRA substrate peptide for the binding to the polyclonal anti active JNK antibody. This can be detected by an increase in fluorescence polarization. The principle of an indirect phosphatase assay is depicted in FIG. 8.

General Example 2C

General Description of a Phosphatase Assay with Monophosphorylated Substrates

In this assay the activity of PPM1E is measured in a phosphatase assay using a monophosphorylated substrate. The substrates may be either monophosphorylated proteins or monophosphorylated peptides which are purified or synthetic substrates. The state of phosphorylation of the substrate is measured after allowing PPM1E to react with the substrate. The change of to phosphorylation of the substrate, the dephosphorylation by the phosphatase PPM1E, the phosphatase activity of PPM1E is determined. The method can be used either in a direct, an indirect or a competitive assay format.
Screening for PPM1E Activity Using Enzymatic Assay of General Example 2A:
List of reagents and buffers of the described phosphatase assays:
Tris buffer: 1 M Tris-HCl, pH 7.5
Dissolve 121.14 g Tris(hydroxymethyl)aminomethan (MW: 121.14, Merck, cat. no. 1.08382.2500) in 1000 ml of Millipore water and adjust to pH to 7.5 with HCl. Buffer should be filtered (0.45 μm) and can be stored at room temperature for several months.
MnCl: 1 M MnCl 4×H2O
Dissolve 19.79 g (MW: 197.91, Sigma-Aldrich, cat. no. M8054-100G) in up to 100 ml of Millipore water. Buffer should be filtered and can be stored at room temperature for several months.
$MgCl_2$: 1 M $MgCl_2$ 6×$H_2O$
Dissolve 20.3 g MgCl2 (MW: 58.44, Merck, cat. no. 1.06404.1000) in up to 100 ml of Millipore water. Buffer should be filtered and can be stored at room temperature for several months.
EDTA: 0.5 M EDTA
Dissolve 18.61 g Ethylenediaminetetraacetic acid disodium salt dehydrate 99+% (MW: 372.24, Sigma, cat. no. E5134-1KG) in up to 100 ml of Millipore water. Buffer should be filtered and can be stored at room temperature for several months.
Tween: 10% Tween 20
Dilute 10 ml Tween 20 ( ) with 90 ml of Millipore water.
Poly(Lys): 1 mg/ml poly(Lys)
Poly-L-Lysine Solution, Sigma-Aldrich, cat. no. P8920. Buffer can be stored at room temperature for several months.
$H_2O_2$: Stock Solution of 8.8 M $H_2O_2$ was Used (Merck, cat. no. 1.07210.0250).
TAMRA-Substrate Peptide Stock Solution: 1 mM 5-TAMRA-MpTPpYV-$NH_2$
A 1 mM stock solution was prepared by dissolving 0.0408 mg 5-TAMRA-MpTPpYV-$NH_2$ (Evotec AG, internal reference number HK07-40-P3-HF) in 34.5 μl 100% DMSO. Aliquots can be stored at –80° C. for several months, short-time storage for up to several weeks at –20° C.
Expression of PPM1E Phosphatase in CCS Sf9 Cells for the Phosphatase Assay:

Full-length His-PPM1E (pFastBac1-vector) has been expressed in Sf9 cells with the Bac-to-Bac system (Invitrogen). Expression was carried out for 72 hours after induction in 500 ml non-adherent cell culture on shakes at 27° C. TC1000 growth medium (GIBCO) was supplemented with 1% sodium pyruvate, 1.5% yeast-extract, 10% FCS (fetal calf serum) and 2% pluronic. The proteins of PPM1E were harvested by sonication of the cells and subsequently purified via His-tag affinity chromatography (His-PPM1E). After this purification the protein species were separated analytically on Bis-Tris chromatographic gels (% gel description) (data not shown). Two major protein species, His-PPM1E full length and the His-PPM1E posttranslationally truncated form (Seq ID NO: 1 and 2) appeared on the gel and were selected and used for the assays, experiments described herein.
Enzyme Solution (His-PPM1E):
The enzyme PPM1E phosphatase was expressed in-house in CCS Sf9 cells with a N-terminal His-tag, affinity-purified over Ni-NTA columns (HisTrap HP, GE Healthcare) and dialysed into the storage buffer. The enzyme is stored at 4° C. Storage buffer: 10 mM Tris-HCl, 150 mM NaCl, pH 7.5. The original PPM1E stock has a concentration of 2.8 μg/μl (33 μM).
Antibody: Polyclonal Anti-Active JNK pAB, Rabbit, (pT-PpY)
Affinity purified polyclonal rabbit IgG Anti-active JNK antibodies (Promega, cat. no. V793A) was supplied in 10 mM sodium phosphate (pH 7.4) containing 20 mM sodium chloride and no preservative. Aliquots of 10 μl can be stored at –80° C. for several months, short-time storage for up to several weeks at –20° C. After thawing, aliquots can be stored at 4° C. for up to several weeks.
Reaction buffer: 50 mM Tris-HCl, 2 mM MnCl, 2 mM $MgCl_2$, 0.1 mM EDTA, 0.01% Tween 20, 10 μg/ml poly(Lys), pH 7.5 at 25° C.
TAMRA Substrate Peptide Solution (5-TAMRA-MpTPpYV-NH2)
1 μM working solution: 5 μl of 100 μM 5-TAMRA-MpTPpYV-NH2, 495 μl reaction buffer.
450 nM working solution (30 nM in 75 μl): 450 μl of 1 μM 5-TAMRA-MpTPpYV-NH2, 550 μl reaction buffer. The solutions were made up freshly and kept on ice.
STOP Solution:
To prepare 0.5 ml stop solution the following reagents were mixed: 8.52 μl H2O2 (8.8 M), 10 μl anti-active JNK pAB (Promega, V793A), 481.48 μl reaction buffer. The solution were prepared immediately before usage and kept on ice.
Experimental Set-Up:
Efficient dephosphorylation of the TAMRA substrate peptide using the direct phosphatase assay is performed as follows: For each reaction at maximum phosphatase activity, 40 μl reaction buffer were mixed with 5 μl 450 nM TAMRA substrate peptide and 5 μl 8 μM enzyme (His-PPM1E) in standard 96 well plates (round bottom). The phosphatase reactions were incubated at 30° C. for 1 hour. Afterwards 25 μl of the STOP solution containing H2O2 and antibodies was added. The mixture was incubated for additional 30 min at room temperature before sample measurements were performed (final reaction).
Sample Measurement:
For measurement, 18 μl of the final reaction was pipetted into a small volume 384 well plate. Reading of the samples was performed on a FCS+plus reader using Two-Dimensional Fluorescence Intensity Distribution Analysis (2D FIDA anisotropy) (Kask et al., Biophysical Journal 2000, 78:1703-1713). Measurement time for controls and samples was 1 s. Controls were measured 10 times, samples one time.

Data Evaluation:

Data were converted with FCS+plus 2.0 Eval software to Excel format and evaluated with Microsoft Excel. The read-out of the PPM1E enzymatic activity assay is the polarisation [mP] observed after a defined reaction time. To evaluate the polarization two measurements are needed: the first using a polarized emission filter parallel to the excitation filter (S-plane) and the second with a polarized emission filter perpendicular to the excitation filter (P-plane). The Fluorescence Polarization response is given as mP (milli-Polarization) level and is obtained from the equation: Polarization (mP)=1000*(S−G*P)/(S+G*P). S and P are background subtracted fluorescence count rates and G (grating) is an instrument and assay dependent factor.

(i) Dephosphorylation of 5-TAMRA-MpTPpYV-NH2 Substrate Peptide by PPM1E Phosphatase Using a Direct Phosphatase Assay.

To determine the optimal enzyme concentration for the PPM1E phosphatase reaction using 5-TAMRA-MpTPpYV-NH2 substrate peptide, kinetic experiments were performed as described in FIG. 9. 45 nM of the labelled TAMRA-substrate peptide were incubated with different enzyme concentrations (0-1.7 µM His-PPM1E) at 30° C. for 60 min. Reactions were stopped with STOP solution ($H_2O_2$ and anti-active JNK antibody) and incubated at room temperature for 30 min to allow the antibody to bind to still fully phosphorylated substrate peptide. A lower polarization indicates a loss of antibody binding to the peptide and therefore a higher PPM1E phosphatase activity (FIG. 9). The original PPM1E phosphatase stock has a concentration of 2.8 µg/µl (33 µM). Dilutions are calculated for the 5 µl enzyme solution (His-PPM1E) that are added during the assay.

(ii) Inhibition of the PPM1E phosphatase-dependent dephosphorylation of TAMRA substrate peptide by the agent-1. The inhibition of PPM1E phosphatase activity was detected using the direct assay and the same experimental set-up as described in Example 2A (i). Testing of the agent-1 was carried out at a constant PPM1E enzyme concentration of 3 µM (final concentration of enzyme before addition of stop solution). The phosphatase activity was measured at different concentrations of the agent-1 (shown in FIG. 10). The polarization rises with higher concentrations of the agent-1, indicating a loss of activity of PPM1E phosphatase.

Example 3

Functional Validation of PPM1E

The reagents and buffers used for the functional validation were the same as described for the assay development (Example 2).

(i) Expression of PPM1E Phosphatase in Neuronal Cell Culture

Full length PPM1E (SEQ ID NO: 1) has been expressed in a H4 neuroglioma cell line (H4) and rat hippocampal primary neuronal cell culture (HC neurons) using the pFB-Neo (Stratagene) and the pAAV vectors (Shevtsova et al., *Experimental Physiology* 2004, 90: 53-59). pFB-Neo contains a CMV-promoter, pAAV a neuron-specific synapsin-promoter which drive the PPM1E expression in the respective cells.

H4 Cell Culture:

H4 cells are cultured in DMEM with 10% FCS. Stable cell lines are prepared by Lipofectamine 2000 transfection of HEK 293 cells (Invitrogen). After 24 hours virus can be harvested and used to infect H4 cells. Under selective pressure of geneticin (400 µg/ml) only cells survive that integrated PPM1E with the CMV promoter and the geneticin resistance gene into their genome. Infected cultures were lysed at 80% confluence with lysis buffer (RIPA buffer (Invitrogen) with protease (Complete, Roche) and phosphatase inhibitor (PhosphoStop, Roche).

Primary Neuronal Cell Culture:

For preparation of hippocampal (HC) rat primary neurons (HC neurons) a pregnant rat is euthanized and the placenta removed. Hippocampi of all feti are dissected under HBSS (Invitrogen) and transferred into plating medium (MEM, 10% FCS, 1% Pen/Strep, 1% Glutamax). Papain (Fluka) is added and after incubation for 12 minutes replaced by fresh medium. HC neurons are resuspended and cells are counted. 75 000 cells are plated/well in 24-well cell culture plates and after adherence the medium is changed to complete medium (Neurobasal, 1% L-Glutamin, 1% Pen/Strep, 2% B27). Medium is changed two times a week Because the transfection rate in primary neurons generally has an efficiency lower than 5%, transfection was only used for the morphological analysis of dendritic spines. To analyse biochemical effects of PPM1E expression, preferably overexpression of PPM1E on HC neurons, a recombinant virus rAAV was prepared by transfection of HEK 293 cells with the pAAV/PPM1E plasmid and the two helper plasmids pDP1 and pDP2 (Shevtsova et al., *Experimental Physiology* 2004, 90: 53-59). Virus was harvested after two days and used for infection of the neuronal culture. This method has an efficiency of more than 90%.

Infection or transfection with Lipofectamine 2000 (Invitrogen) of primary neurons was carried out at day-in-vitro (DIV) 7. The cultures were evaluated on DIV21. Infected cultures were lysed on DIV21 with lysis buffer (RIPA buffer (Invitrogen) with protease (Complete, Roche) and phosphatase inhibitor (PhosphoStop, Roche). Transfected cultures were fixed in 4% formaldehyde with 4% sucrose on DIV21 for 10 min and afterwards analysed at a confocal microscope.

(ii) Activity of PPM1E Phosphatase in Neuronal Cells

Biochemical Analysis:

The phosphatase activity of PPM1E was analyzed biochemically in H4 neuroglioma cell lines and primary hippocampal rat cell cultures.

Protein expression levels of PPM1E and CaMKII and the phosphorylation status of CaMKII were analysed with western blotting techniques. Detection of western blot signals was carried out with ECF or Qdot detection systems (Invitrogen) on a fluorescence scanner, which allowed a sensitive quantification of the bands that appeared on the blots. Full length-expressed PPM1E appears on all blots as a mixture of full-length and of post-translationally truncated PPM1E.

CaMKII has several isoforms, the isoform CaMKII beta isoform has a size of 57 kDa, the alpha isoform of 50 kDa, and both are detected by the phosphorylation specific antibody ab32678 (abcam) which detects phosphorylated threonine at amino acid position 286 (Thr286) of CaMKII. Generally, the phosphorylation of both isoforms has been quantified together as shown in FIG. 11A (highlighted with a box). Phosphorylation of CaMKII is reduced by PPM1E in H4 cells and primary HC neurons showing the activity of PPM1E. Additionally, it was shown that PPM1E is dephosphorylating both isoforms, by quantifying the bands separately (FIG. 13). The level of the CaMKII kinases themselves were constant during all experiments (data not shown).

Morphological Analysis:

The phosphatase activity of PPM1E was analyzed morphologically in primary hippocampal rat cell cultures. Synaptic damage reflects neurodegeneration and is a very early pathological hallmark of many neurological disorder like e.g. Alzheimer's disease (Selkoe D J, Science 2002, 298). Therefore it was examined whether PPM1E phosphatase impairs synaptic integrity and function in primary rat neuronal cell culture.

For this purpose rat primary neurons were co-transfected in 24 well cell culture plates on day-in-vitro 7 (DIV7) with 0.2 μg pAAV/GFP and 0.2 μg pAAV/PPM1E/well. Transfections using 0.2 μg GFP only/well were used as negative controls. On DIV21 confocal stacks of 30 neurons (63× magnification and 2× zoom) were taken. In the reconstituted stacks the number of dendritic spines per μm dendrite on two secondary dendrites per neuron were counted. The results are shown in FIGS. 15 and 16 and verify that PPM1E expression leads to a reduction in the number of dendritic spines, in a reduction of spine density, which indicate a loss of synaptic integrity of the neurons.

---

The invention claimed is:

1. A method for identifying putative agents for the treatment of Alzheimer's disease, said method comprising:
   (a) contacting an agent with a phosphorylated substrate and with a protein phosphatase 1 E having SEQ ID NO:1 or SEQ ID NO:2,
   (b) measuring the enzymatic activity of said protein phosphatase 1 E having SEQ ID NO:1 or SEQ ID NO:2,
   (c) comparing the enzymatic activity measured in step (b) with the enzymatic activity of a protein phosphatase 1 E having SEQ ID NO:1 or SEQ ID NO:2 not contacted with said agent,
   (d) identifying agents that decrease the enzymatic activity of said protein phosphatase 1 E having SEQ ID NO:1 or SEQ ID NO:2 as putative agents for the treatment of Alzheimer's disease.

2. A method for identifying putative agents for the treatment of Alzheimer's disease, said method comprising:
   (a) contacting a sample comprising an expression system for expression of a protein phosphatase 1 E having SEQ ID NO:1 or SEQ ID NO:2 with an agent
   (b) measuring the expression level of the gene coding for a protein phosphatase 1 E having SEQ ID NO:1 or SEQ ID NO:2, and/or a transcription product of the gene coding for protein phosphatase 1 E having SEQ ID NO:1 or SEQ ID NO:2 in said sample
   (c) comparing the expression level measured in step (b) with the expression level of a gene coding for a protein phosphatase 1 E having SEQ ID NO:1 or SEQ ID NO:2, and/or a transcription product of the gene coding for a protein phosphatase 1 E having SEQ ID NO:1 or SEQ ID NO:2 measured in a sample comprising an expression system for expression of a protein phosphatase 1 E having SEQ ID NO:1 or SEQ ID NO:2 not contacted with said agent,
   (d) identifying agents that decrease the expression level of a gene coding for a protein phosphatase 1 E having SEQ ID NO:1 or SEQ ID NO:2, and/or a transcription product of the gene coding for a protein phosphatase 1 E having SEQ ID NO:1 or SEQ ID NO:2 as putative agents for the treatment of Alzheimer's disease.

3. A method for identifying putative agents for the treatment of Alzheimer's diseases, said method comprising:
   (a) contacting a neuronal cell which expresses a protein phosphatase 1 E having SEQ ID NO:1 or SEQ ID NO:2 with an agent
   (b) determining the number of dendritic spines and/or dendritic spine density in said cell
   (c) comparing the number of dendritic spines and/or the dendritic spine density determined in step (b) with the number of dendritic spines and/or dendritic spine density in a cell which expresses a protein phosphatase 1 E having SEQ ID NO:1 or SEQ ID NO:2 not contacted with said agent,
   (d) identifying agents that increase the number of dendritic spines and/or dendritic spine density as putative agents for the treatment of Alzheimer's disease.

* * * * *